(12) United States Patent
Isomura et al.

(10) Patent No.: US 9,395,325 B2
(45) Date of Patent: Jul. 19, 2016

(54) GAS SENSOR

(71) Applicant: NGK SPARK PLUG CO., LTD., Nagoya-shi, Aichi-ken (JP)

(72) Inventors: Hiroshi Isomura, Nagoya (JP); Katsuyoshi Hidaka, Kitanagoya (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 539 days.

(21) Appl. No.: 13/901,125

(22) Filed: May 23, 2013

(65) Prior Publication Data

US 2013/0334043 A1 Dec. 19, 2013

(30) Foreign Application Priority Data

May 24, 2012 (JP) ................................. 2012-118959
Apr. 15, 2013 (JP) ................................. 2013-084999

(51) Int. Cl.
*G01N 27/409* (2006.01)
*G01N 27/406* (2006.01)

(52) U.S. Cl.
CPC .......... *G01N 27/409* (2013.01); *G01N 27/4067* (2013.01)

(58) Field of Classification Search
CPC ........... G01N 27/406–27/407; G01N 27/4073; G01N 27/41
See application file for complete search history.

(56) References Cited

U.S. PATENT DOCUMENTS 6,354,134 B1   3/2002   Katafuchi et al.

FOREIGN PATENT DOCUMENTS

| JP | 56-90256 A | 7/1981 |
|---|---|---|
| JP | 57-166556 A | 10/1982 |
| JP | 2000-081411 A | 3/2000 |
| JP | 2003-287516 A | 10/2003 |
| JP | 2003-322631 A | 11/2003 |

OTHER PUBLICATIONS

Communication dated Mar. 3, 2015 from the Japanese Patent Office in counterpart Application No. 2013-084999.

*Primary Examiner* — J. Christopher Ball
(74) *Attorney, Agent, or Firm* — Sughrue Mion, PLLC

(57) ABSTRACT

A gas sensor including a detection element (6), wherein a detection electrode (63D) and a reference electrode (62B) are provided on an outer circumferential surface (61A) and an inner circumferential surface, respectively, of a closed-bottomed tubular solid electrolyte body (61). A heater inserted into the tubular hole of the detection element (6) is in contact with the reference electrode at point Q. The detection electrode (63D) is partially formed in the vicinity of a position which faces the point Q with the solid electrolyte body (61) intervening therebetween, and the surface area of the detection electrode (63D) is 8% to 20% of the surface area of a detection portion (64).

13 Claims, 15 Drawing Sheets

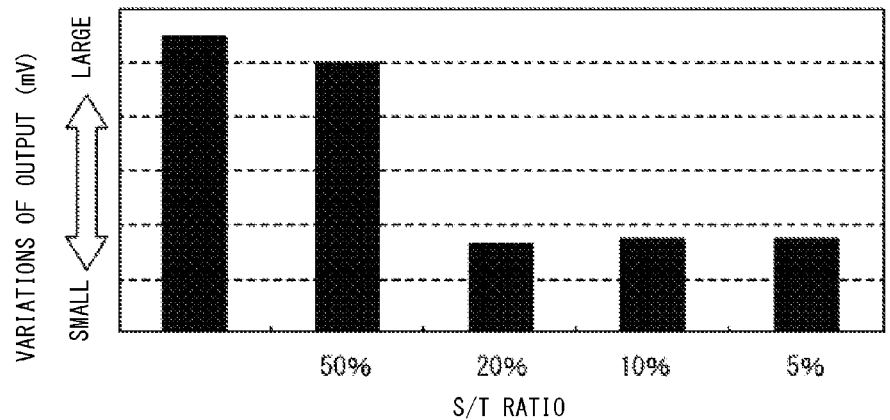
FIG. 16
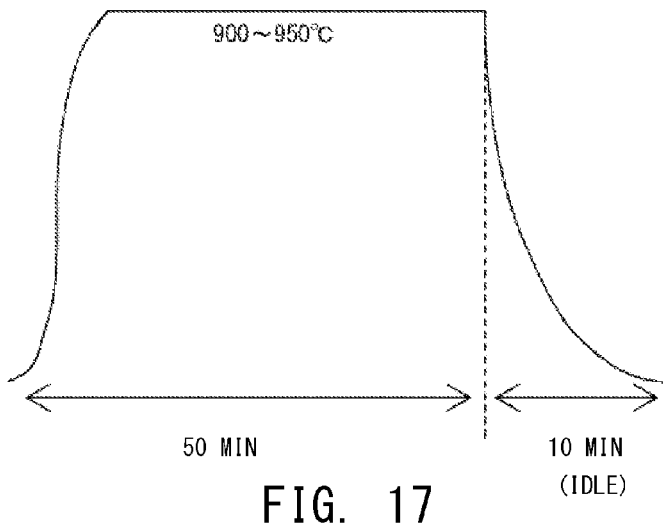
FIG. 17
| | | DURABILITY TIME | | |
|---|---|---|---|---|
| | | 1000h | 2000h | 3000h |
| S/T RATIO | 5% | POOR | POOR | NOT CARRIED OUT |
| | 8% | GOOD | GOOD | GOOD |
| | 50% | GOOD | GOOD | GOOD |
| | CONVENTIONAL | NOT CARRIED OUT | NOT CARRIED OUT | GOOD |
FIG. 18

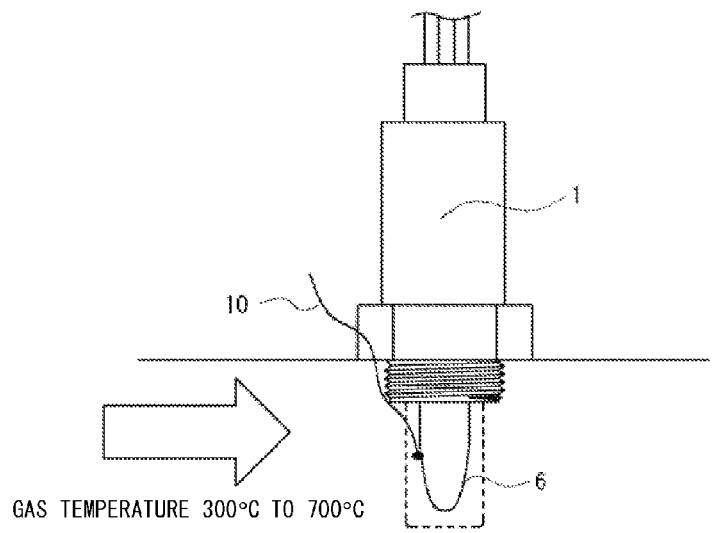
FIG. 19
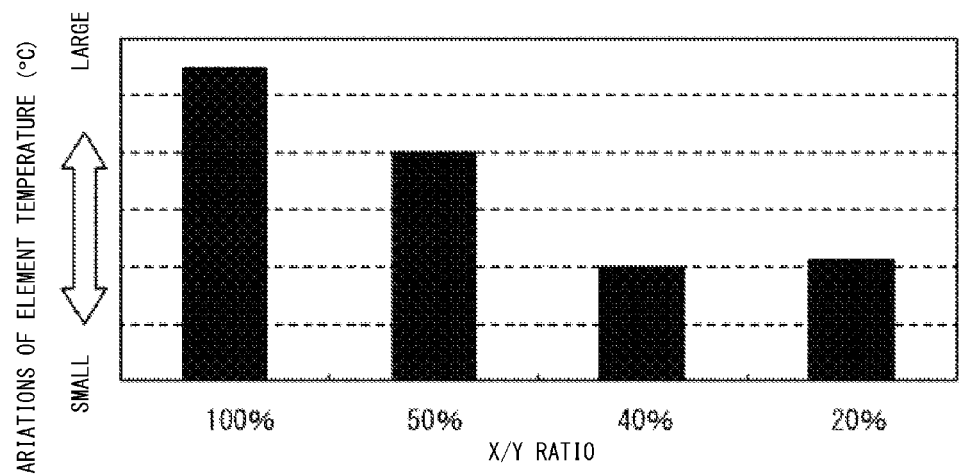
FIG. 20
| ANGLE θ | 180° | 160° | 100° | 50° |
|---|---|---|---|---|
| PLATING BLUR | × | ○ | ○ | ○ |
FIG. 21

GAS SENSOR

TECHNICAL FIELD

The present invention relates to a gas sensor having a detection element for detecting the concentration of a particular gas contained in gas to be measured.

BACKGROUND ART

Conventionally, the detection element of a gas sensor used to detect the concentration of a particular gas contained in gas to be detected is formed of ceramic, such as zirconia, and is formed such that a closed-bottomed tubular solid electrolyte body having a closed end intervenes between a pair of electrodes. The pair of the electrodes is formed of, for example, platinum or a platinum alloy. Also, a pair of lead wires is electrically connected to the pair of electrodes for leading out output of the detection element. A heater having, at its forward end portion, a heat-generating resistor for generating heat through energization is disposed within a forward portion of the detection element for activating the solid electrolyte body through application of heat.

Such a detection element detects a particular gas component (e.g., oxygen) contained in gas taken in or exhausted from an internal combustion engine of an automobile or the like. For example, in an oxygen sensor for detecting oxygen contained in exhaust gas from an internal combustion engine of an automobile or the like, a pair of electrodes consists of a measuring electrode exposed to exhaust gas and a reference electrode exposed to reference gas (usually, the air), and the pair of electrodes is formed on the surface of the closed-bottomed tubular solid electrolyte body such that the solid electrolyte body intervenes between the electrodes. A forward portion of the solid electrolyte body is exposed to exhaust gas. The solid electrolyte body is activated through application of heat from the heater. On the basis of electromotive force which is generated between the two electrodes according to a difference in partial pressure of oxygen between exhaust gas and reference gas (the air), the detection element detects oxygen contained in exhaust gas and provides output outward through a pair of lead wires.

A gas sensor having such a structure is required, even when the solid electrolyte body is partially inactive as a result of failure to receive a sufficient amount of heat from the heater, to be free from its influence on output of the detection element. Furthermore, the gas sensor is required, even when an electrode portion sublimates as a result of application of heat from the heater, to exhibit high durability so as to be resistant to consumption of the electrode portion caused by the sublimation. Accordingly, there is known a gas sensor in which the measuring electrode provided on the outer circumferential surface of the solid electrolyte body is formed along the full circumference of the solid electrolyte body at a forward end portion of the detection element and reduces in its circumferential range of formation toward the rear end of the detection element and in which the heater is in contact with the inner circumferential wall of a forward end portion of the solid electrolyte body (refer to, for example, Patent Document 1). According to the invention described in Patent Document 1, a high-temperature region appears at a forward end portion of the solid electrolyte body because of the contact of the heater; however, the range of formation of the electrode reduces with distance from the high-temperature region. Thus, when the detection element provides output outward, influence of an inactive region of the solid electrolyte body can be reduced. At the same time, the range of formation of the measuring electrode is large at a forward end portion of the solid electrolyte body where a high-temperature region appears; therefore, the measuring electrode is resistant to consumption caused by sublimation. Accordingly, the gas sensor has high durability against heat.

PRIOR ART DOCUMENT

Patent Document

[Patent Document 1] Japanese Patent Application Laid-Open (kokai) No. 2003-322631

SUMMARY OF THE INVENTION

Problems to be Solved by the Invention

Now, output of the detection element is desirably constant; therefore, the activated solid electrolyte body must be controlled at a fixed temperature. According to a known control method for such control, an external control unit provided externally of a gas sensor applies current to the solid electrolyte body and thereby detects and controls the temperature of the solid electrolyte body. Specifically, the external control unit applies electricity to the solid electrolyte body through a pair of electrodes and detects the resistance of the solid electrolyte body. On the basis of the detected resistance, the external control unit detects the temperature of the solid electrolyte body. On the basis of a difference between the detected temperature of the solid electrolyte body and an intended temperature, the external control unit adjusts application of electricity to the heat-generating resistor, thereby adjusting heating performed by the heater. By this procedure, the solid electrolyte body assumes the intended temperature and is maintained at the temperature.

However, according to the invention described in Patent Document 1, as shown in FIG. 14, which is a sectional view of a solid electrolyte body 61 taken along a plane in parallel with a radial direction of the solid electrolyte body 61, since the vicinity region of a contact portion (point Q in FIG. 14) of the solid electrolyte body 61 in contact with a heater 100 and the other region of the solid electrolyte body 61 differ in distance to a heat-generating portion of the heater 100 where a heater pattern is formed, at the time of heating by the heater, a difference in temperature rise may arise therebetween. Particularly, in the case where gas to be detected in contact with a detection element 6 is low in temperature, a region of the solid electrolyte body 61 which is not in contact with the heater 100 fails to sufficiently rise in temperature, so that a temperature difference arises. Meanwhile, the temperature of the solid electrolyte body 61 is calculated on the basis of resistance detected from the current which flows as a result of application of electricity to a pair of electrodes. That is, temperature is determined from a combined resistance of a region of the solid electrolyte body 61 intervening between the pair of electrodes. However, in the case where a detection electrode 63D is formed along the full circumference of the solid electrolyte body 61, since electricity is also applied to a region which is not in contact with the heater 100, a calculated temperature becomes lower than the temperature of the contact portion in contact with the heater 100. That is, in the case where gas to be detected in contact with the detection element 6 is low in temperature, even though the external control unit detects the current, the external control unit may fail to accurately perform temperature control of the solid electrolyte body 61.

The present invention has been conceived in view of the above problem, and an object of the present invention is to provide a gas sensor which has high durability against heat and which allows accurate temperature control of the solid electrolyte body without being influenced by an inactive region of the solid electrolyte body and by the temperature of gas to be detected when the detection element provides output.

Means for Solving the Problems

A first mode of the present invention provides a gas sensor to be exposed to gas to be measured, comprising a sensor element having a closed-bottomed tubular solid electrolyte body having a closed forward end and extending in a direction of an axis, an outer electrode portion provided on an outer surface of a forward end portion of the solid electrolyte body, and an outer lead portion extending rearward from the outer electrode portion in the direction of the axis and having a circumferential width narrower than a width of a rear end region of the outer electrode portion, and a heater having a heat-generating portion formed of a heat-generating resistor which generates heat through application of electricity, and being in contact with an inner surface of the sensor element, the gas sensor being characterized in that the outer electrode portion has at least an outer partial electrode portion formed partially with respect to a circumferential direction of the outer surface, and the outer electrode portion is disposed at such a position as to face a contact portion of the inner surface of the sensor element in contact with the heater with the solid electrolyte body intervening therebetween, and a surface area S of the outer electrode portion is 8% to 20% of a surface area T of a gas contact portion of the solid electrolyte body to be exposed to the gas to be measured.

In the present mode, the range of formation of the outer electrode portion is limited to the vicinity of the heater contact portion while the relation of S being 8% to 20% of T is maintained. Thus, even when the temperature of the solid electrolyte body heated by the heater differs from region to region, current which flows when electricity is applied to the solid electrolyte body through the outer electrode portion reflects only the resistance of a region of the solid electrolyte body which is in the vicinity of the heater contact portion and is most activated. Therefore, the external control unit which is provided externally of the gas sensor and controls the temperature of the solid electrolyte body through application of current to the solid electrolyte body and to the heater can accurately detect the temperature of the solid electrolyte body only in a region in the vicinity of the heater contact portion and thereby can accurately control the temperature of the solid electrolyte body. That is, even when the temperature of the solid electrolyte body differs from region to region, the external control unit can accurately perform temperature control of the solid electrolyte body without being influenced by the temperature of gas to be detected; thus, the gas sensor can provide constant output. At the same time, at the time of heating by the heater, even when the solid electrolyte body has an inactive region, the gas sensor is free from influence of the inactive region since the range of formation of the outer electrode portion is limited more than in the case of a conventional practice. That is, the response performance of the gas sensor is improved. Furthermore, since the minimum amount of formation against heat can be secured for the outer electrode portion, the outer electrode portion can be resistant to consumption caused by sublimation. That is, the gas sensor can achieve high durability against a high temperature.

In the present mode, the outer partial electrode portion may be disposed at such a position as to face the contact portion of the inner surface of the sensor element in contact with the heater with the solid electrolyte body intervening therebetween. In this case also, the above-mentioned effect can be yielded.

A second mode of the present invention provides a gas sensor to be exposed to gas to be measured, comprising a heater having a heat-generating portion formed of a heat-generating resistor which generates heat through application of electricity, a sensor element having a closed-bottomed tubular solid electrolyte body having a closed forward end and extending in a direction of an axis, an outer electrode portion provided on an outer surface of a forward end portion of the solid electrolyte body on a forward side of a rear end of the heat-generating portion with respect to the direction of the axis, and an outer lead portion extending rearward from the outer electrode portion in the direction of the axis and having a width equal to a width of the outer electrode portion, the gas sensor being characterized in that the heater is in contact with an inner surface of the sensor element, the outer electrode portion is formed partially with respect to a circumferential direction of the outer surface of the solid electrolyte body, the outer electrode portion is disposed at such a position as to face a contact portion of the inner surface of the sensor element in contact with the heater with the solid electrolyte body intervening therebetween, and a surface area S of the outer electrode portion is 8% to 20% of a surface area T of a gas contact portion of the solid electrolyte body to be exposed to the gas to be measured.

Even in the case where the outer electrode portion and the outer lead portion have the same width, the above-mentioned effect can be yielded.

In the first and second modes, as viewed from the direction of the axis, of angles formed by a line segment connecting two points; i.e., one circumferential end of the outer electrode portion and a center of the solid electrolyte body, and a line segment connecting two points; i.e., the other circumferential end of the outer electrode portion and the center, an angle in a region which contains the outer electrode portion may be less than 180°. Generally, in order to form the outer electrode portion on the outer surface of the solid electrolyte body, the manufacturing process involves a plating process in which the solid electrolyte body is immersed in a plating solution. Before immersion in the plating solution, a mask is attached to an outer surface of the solid electrolyte body on which the outer electrode portion is not to be formed. In the case of the present modes, the outer electrode portion is formed along a circumferential range which is equal to or less than half of the circumference of the solid electrolyte body. That is, the mask covers the solid electrolyte body along a circumferential range which is equal to or greater than half of the circumference of the solid electrolyte body. Thus, the mask attached to the solid electrolyte body has sufficient force of gripping the solid electrolyte body, so that the inner circumferential surface of mask rubber and the outer surface of the solid electrolyte body can be in sufficiently close contact with each other. Therefore, the gas sensor according to the present modes can prevent, in the plating process, entry of the plating solution between the inner circumferential surface of mask rubber and the outer surface of the solid electrolyte body.

In the first and second modes, with respect to the direction of the axis, a length from a forward end of the gas contact portion to a rear end of the outer electrode portion may be 40% or less of a length of the gas contact portion. In this case, the outer electrode portion is provided in such a manner as to cover the heat-generating portion of the heater in the vicinity of the heater contact portion. Therefore, the outer electrode portion is provided reliably at a region of the solid electrolyte body which is most activated when the heater generates heat; i.e., at a region in the vicinity of the heater contact portion and the heat-generating portion of the heater. Thus, the external control unit can reliably detect a highest temperature of the solid electrolyte body and can thereby perform temperature control of the solid electrolyte body reliably and accurately without being influenced by the temperature of gas to be measured.

In the first and second modes, the gas sensor may further comprise an inner electrode portion provided on an inner surface of a forward end portion of the solid electrolyte body, and with respect to the direction of the axis, a rear end of the inner electrode portion may be located rearward of a rear end of the outer electrode portion. In this case, the rear end of the inner electrode portion is located forward of the rear end of the outer electrode portion, whereby there can be prevented the occurrence of variations of element surface temperature which could otherwise result from the rear end of the inner electrode portion being located forward of the rear end of the outer electrode portion.

In the first and second modes, the inner electrode portion may have at least an inner partial electrode portion formed partially with respect to a circumferential direction of the inner surface, and the inner partial electrode portion may be disposed at such a position as to face at least partially the outer partial electrode portion with the solid electrolyte body intervening therebetween. In this case, the inner partial electrode portion and the outer partial electrode portion are disposed in such a mutually facing manner as to face each other at least partially, and the heater is in contact with its vicinity; therefore, element activating time can be shortened.

In the first and second modes, the heater may be in contact with an inner side surface of an inner surface of the sensor element. In this case, even in the case where the heater is in contact with the inner surface of the sensor element, effects similar to those yielded by the first and second modes can be yielded.

BRIEF DESCRIPTION OF THE DRAWINGS

FIG. 16 Table showing the results of the test for variations of output of the oxygen sensor 1.
FIG. 17 Graph showing the conditions of a durability test on the oxygen sensor 1.
FIG. 18 Table showing the results of the durability test on the oxygen sensor 1.
FIG. 19 View showing a method of a test for variations of temperature of the detection element 6 of the oxygen sensor 1.
FIG. 20 Table showing the results of the test for variations of temperature of the detection element 6 of the oxygen sensor 1.
FIG. 21 Table showing the results of the plating process.

MODES FOR CARRYING OUT THE INVENTION

Figure 1:
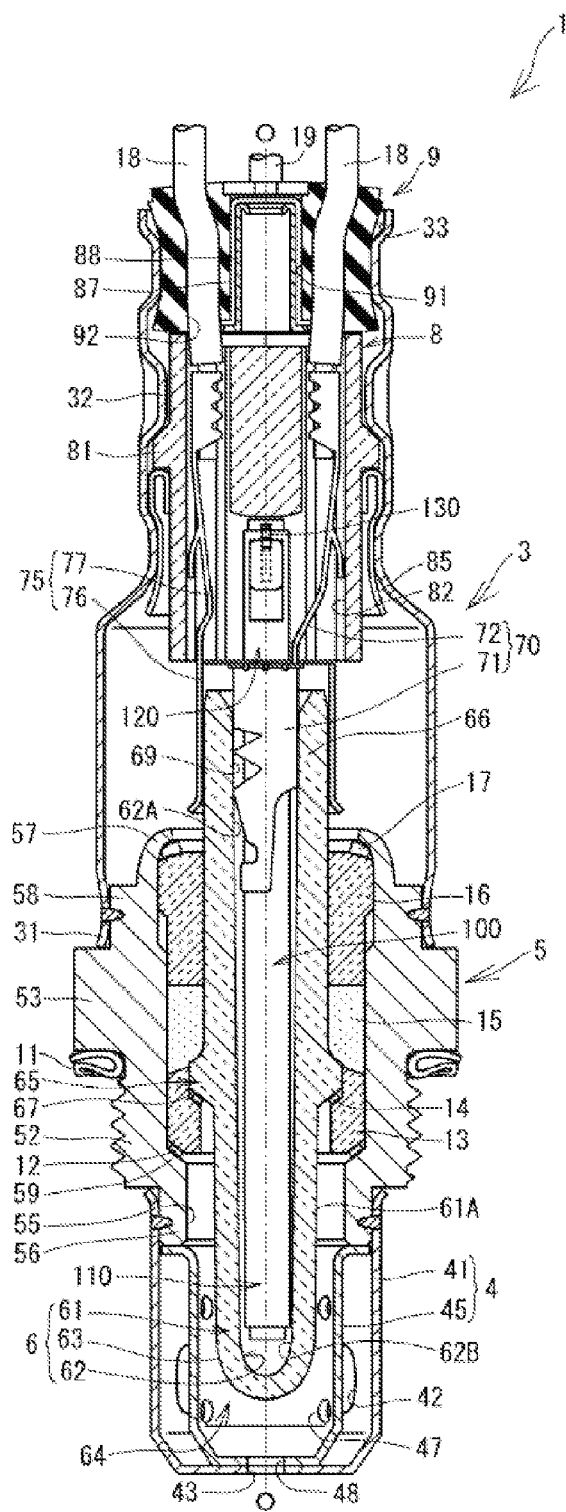
FIG. 1 Longitudinal, sectional view of an oxygen sensor 1.

An oxygen sensor according to a first embodiment of the present invention will next be described with reference to the drawings. With reference to FIG. 1, the entire configuration of an oxygen sensor 1 is described by way of example. The drawings referred to are used merely to explain technical features which the present invention can employ. The configuration of the oxygen sensor 1, etc., are mere examples for explanation and should not be construed as limiting the invention. In the following description, the front side, the back side, the upper side, the lower side, the right side, and the left side of the paper on which FIG. 1 appears are defined as the left side, the right side, the upper side (rear side), the lower side (forward side), the front side, and the far side, respectively, of the oxygen sensor 1.

The oxygen sensor 1 shown in FIG. 1 is attached, for use, to an exhaust pipe (not shown) for exhaust gas exhausted from an internal combustion engine of an automobile or the like and is adapted to detect whether or not oxygen is contained in exhaust gas which flows through the exhaust pipe. In attachment of the oxygen sensor 1, a forward portion of a detection element 6 located at the forward side (lower side) of the oxygen sensor 1 is inserted into the exhaust pipe (not shown). The direction of an axis O of the oxygen sensor 1 shown in FIG. 1 is in parallel with the vertical direction.

As shown in FIG. 1, the oxygen sensor 1 has a structure in which a metallic shell 5 surrounds and holds the tubular detection element 6 having a closed forward end. Two lead wires 18 extend outward from the oxygen sensor 1 for leading out signals output from the detection element 6. Also, two lead wires 19 (FIG. 1 shows one of them) extend outward from the oxygen sensor 1 for applying electricity to the heater 100 inserted into the detection element 6. The lead wires 18 and 19 are electrically connected to an unillustrated external circuit (e.g., the electronic control unit (ECU) of an automobile) provided at a position located away from the oxygen sensor 1. The present embodiment uses, by way of example, the electronic control unit (ECU) as an external circuit.

Figure 2:
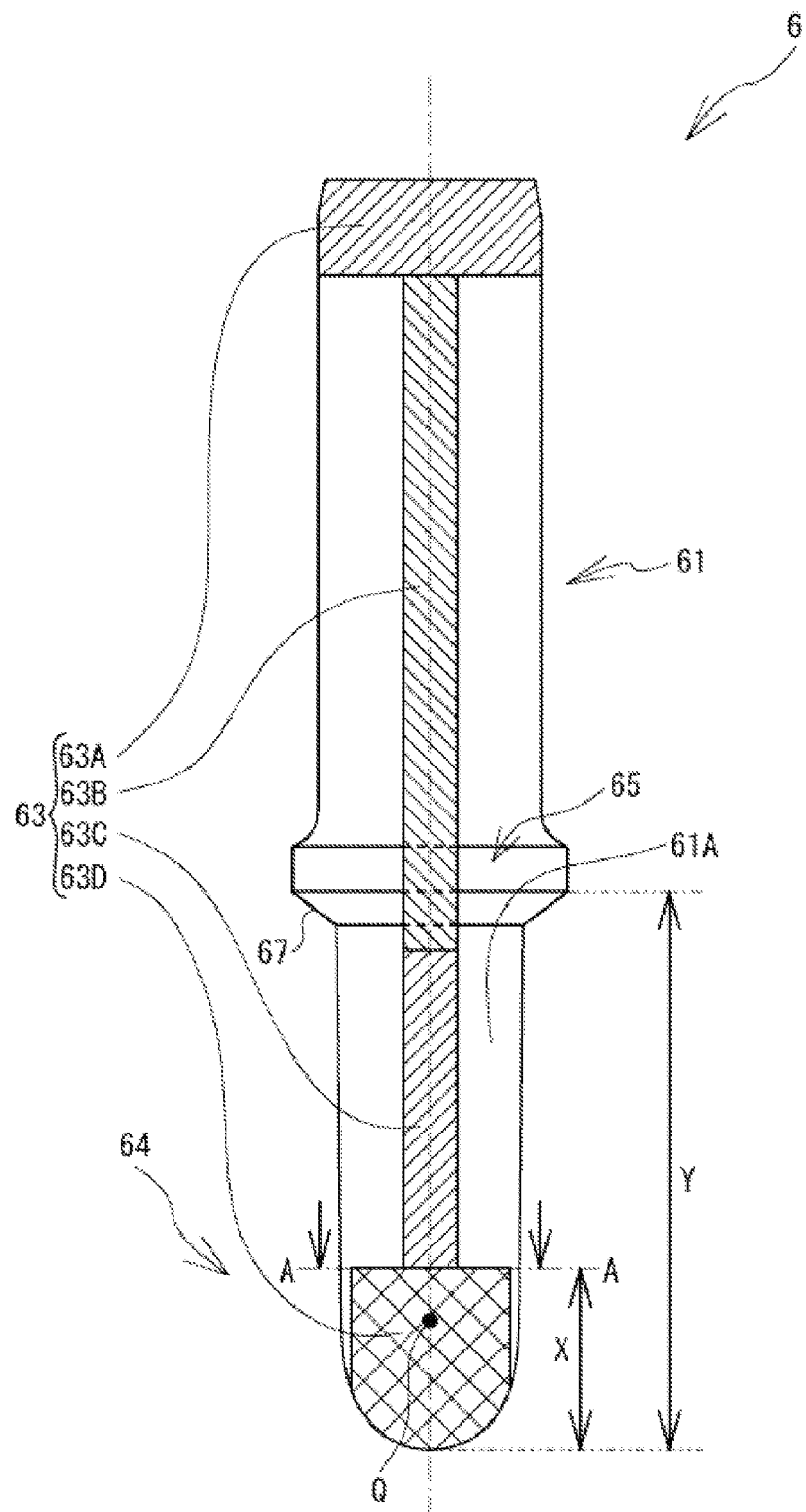
FIG. 2 Front view of a detection element 6.
Figure 3:
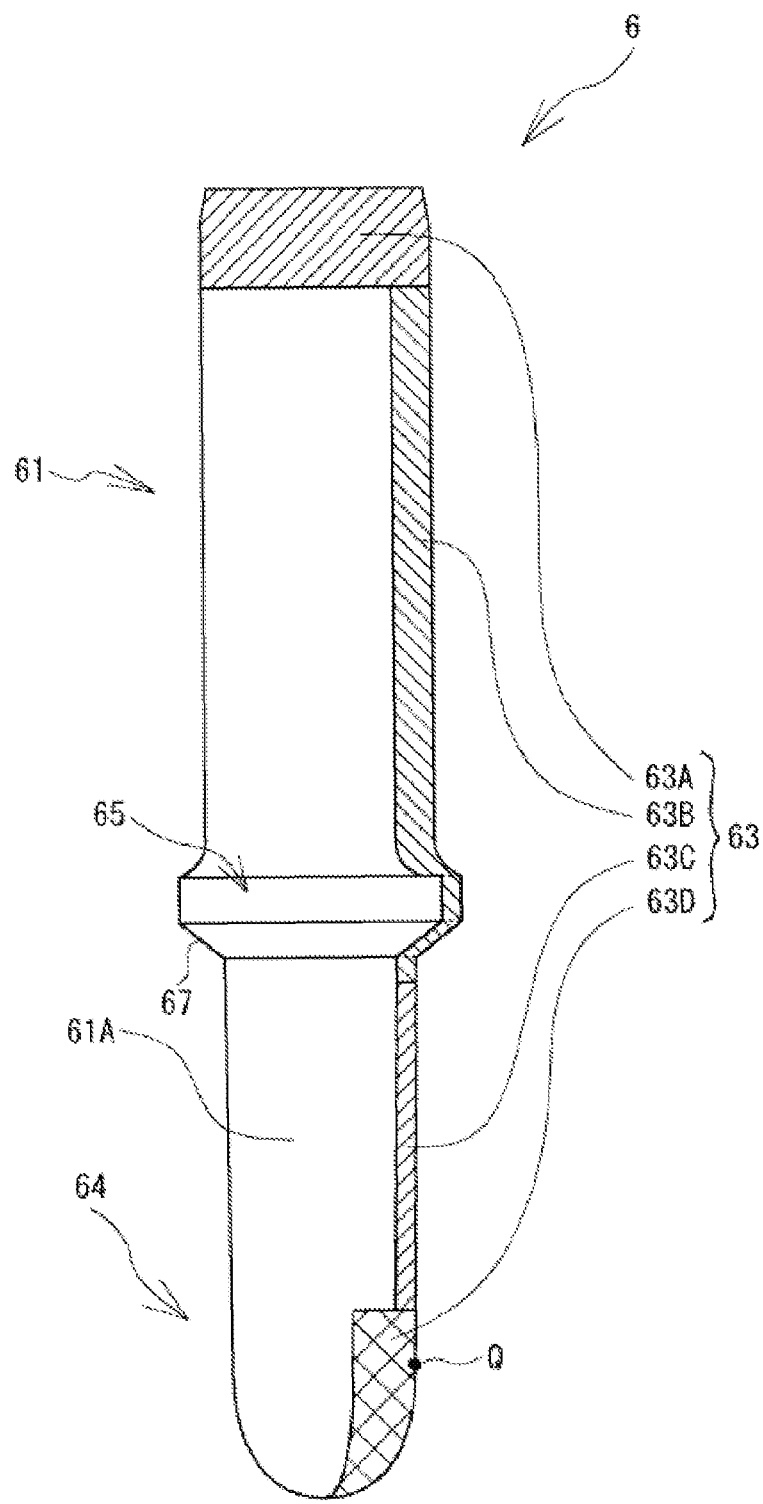
FIG. 3 Left side view of the detection element 6.

First, with reference to FIGS. 1 to 3, the detection element 6 will be described. As shown in FIG. 1, the detection element 6 includes a closed-bottomed tubular solid electrolyte body 61 extending in the direction of the axis O and having a closed forward end; a reference electrode portion 62 provided on the inner circumferential surface (inner surface) of the solid electrolyte body 61; and a detection electrode portion 63 provided on an outer circumferential surface 61A of the solid electrolyte body 61. A tubular hole 69 is formed through provision of the reference electrode portion 62 on the inner circumferential surface (inner surface) of the solid electrolyte body 61. The solid electrolyte body 61 contains zirconia as a main component and has a collar-like flange portion 65 extending radially outward and provided at a substantially middle position with respect to the direction of the axis O. As shown in FIGS. 2 and 3, a detection portion 64 extends from the rear end of a diameter-expanding portion 67, which is a portion of the flange portion 65 and whose diameter expands rearward from its forward end, to the forward end of the solid electrolyte body 61. When the oxygen sensor 1 is attached to the exhaust pipe (not shown), only the detection portion 64 of the solid electrolyte body 61 is exposed to the interior of the exhaust pipe.

As shown in FIG. 1, the reference electrode portion 62 includes a lead portion 62A and a reference electrode 62B. The lead portion 62A formed of platinum or a platinum alloy is porously formed on the inner circumferential surface of a rear portion of the solid electrolyte body 61. The reference electrode 62B formed of platinum or a platinum alloy is porously formed in such a manner as to cover the inner circumferential surface of a portion of the solid electrolyte body 61 located forward of the lead portion 62A. Similarly, the detection electrode portion 63 is formed of platinum or a platinum alloy and is, as shown in FIGS. 2 and 3, porously formed on a portion of the outer circumferential surface 61A of the solid electrolyte body 61. The configuration of the detection electrode portion 63 and the range of formation of the detection electrode portion 63 on the outer circumferential surface 61A are described later. The detection electrode portion 63 is covered with a porous electrode protection layer (not shown) formed of heat-resistant ceramic and is thereby protected from poisoning by exhaust gas. As shown in FIG. 1, the reference electrode portion 62 and the detection electrode portion 63 are electrically connected to the corresponding lead wires 18 via an inner terminal 70 and an outer terminal 75, respectively, which will be described later. Thus, when the detection portion 64 is exposed to exhaust gas flowing through the exhaust pipe (not shown), the detection element 6 can detect oxygen concentration.

As shown in FIG. 1, the metallic shell 5 circumferentially surrounds and holds the detection element 6 in its tubular hole 55. The metallic shell 5 is a tubular member formed of stainless steel, such as SUS430, and has an externally threaded portion 52 which is formed on its forward portion and is threadingly engaged with an attachment portion (not shown) of the exhaust pipe. The metallic shell 5 has a forward-end attachment portion 56 which is formed on its outer circumference on a forward side of the externally threaded portion 52 and to which a protector 4, which will be described later, is fitted and attached. A forward end portion of the detection portion 64 of the detection element 6 protrudes forward from the forward-end attachment portion 56.

The metallic shell 5 has a radially expanded tool engagement portion 53 formed on the rear side of the externally threaded portion 52, and an attaching tool is engaged with the tool engagement portion 53 when the oxygen sensor 1 is to be attached to an attachment portion (not shown) of the exhaust pipe. An annular gasket 11 is fitted to a region between the tool engagement portion 53 and the externally threaded portion 52 for preventing gas release via the attachment portion of the exhaust pipe. Additionally, the metallic shell 5 has a crimped portion 57 provided at its rear end for fixing the detection element 6 held within the tubular hole 55, through a ring 17, a sleeve 16, a filling member 15, a packing 14, a support member 13, etc., which will be described later. A rear end portion 66 of the detection element 6 protrudes rearward from the crimped portion 57. Also, the metallic shell 5 has a rear-end engagement portion 58 formed on its outer circumference between the tool engagement portion 53 and the crimped portion 57 for allowing a forward end portion 31 of a tubular housing 3, which will be described later, to be engaged therewith.

Next, the metallic shell 5 has a stepped portion 59 provided at a forward end portion of the tubular hole 55 and formed through radially inward protrusion of the inner circumference of the forward end portion. The tubular support member 13 formed of alumina is seated on the stepped portion 59 via a packing 12 made of metal. The support member 13 also has a stepped portion formed on its inner circumference, and the diameter-expanded portion 67 of the flange portion 65 of the detection element 6 abuts against the stepped portion via the packing 14 made of metal. Through this configuration, the support member 13 supports the detection element 6. Furthermore, the filling member 15 of a talc powder is charged into the tubular hole 55 on the rear side of the support member 13. The tubular sleeve 16 formed of alumina is disposed on the rear side of the filling member 15 in such a manner that the filling member 15 is sandwiched between the same and the support member 13.

The annular ring 17 is disposed on the rear side of the sleeve 16. As a result of inward, forward crimping of the crimped portion 57 of the metallic shell 5, the sleeve 16 is pressed against the filling member 15 via the ring 17. As a result of crimping of the crimped portion 57, the filling member 15 is compressively filled into the tubular hole 55 of the metallic shell 5 in such a manner as to press the flange portion 65 of the detection element 6 toward the support member 13 seated on the stepped portion 59 of the metallic shell 5. A gap between the inner circumferential surface of the tubular hole 55 and the outer circumferential surface of the detection element 6 is airtightly filled with the filling member 15. In this manner, the detection element 6 is held within the tubular hole 55 of the metallic shell 5 via the members held between the crimped portion 57 and the stepped portion 59 of the metallic shell 5.

As mentioned above, a forward end portion of the detection portion 64 protrudes forward from the forward-end attachment portion 56 of the metallic shell 5 along the direction of the axis O. Also, the detection portion 64 is covered with the protector 4 welded to the forward-end attachment portion 56. The protector 4 protects the detection portion 64 of the detection element 6 which protrudes into the exhaust pipe when the oxygen sensor 1 is attached to the exhaust pipe (not shown), from impact of water droplets, foreign matter, etc., contained in exhaust gas. The protector 4 has a dual structure consisting of an outer protector 41 and an inner protector 45. The outer protector 41 has a closed-bottomed tubular shape, and a peripheral portion of its open end is joined to the forward-end attachment portion 56. Similarly, the inner protector 45 has a closed-bottomed tubular shape and is fixed in the interior of the outer protector 41. The outer protector 41 and the inner protector 45 have introduction ports 42 and 47 which open at their outer circumferential surfaces, respectively, for introducing exhaust gas therein and to the detection portion 64 of the detection element 6. The outer protector 41 and the inner protector 45 also have discharge ports 43 and 48 which open at their bottoms, respectively, for discharging water droplets and exhaust gas which have entered therein.

Next, the tubular housing 3 formed of stainless steel, such as SUS304, is attached to a rear end portion of the metallic shell 5. The tubular housing 3 is formed as follows: stainless steel is formed into a tubular shape extending along the direction of the axis O such that a portion extending forward substantially from the center is greater in diameter than a rear portion. The forward end portion 31 of the tubular housing 3 is fitted to the rear-end engagement portion 58 of the metallic shell 5 and is crimped from its outer circumference to the rear-end engagement portion 58. Furthermore, laser welding is performed along the entire outer circumference of the forward end portion 31. The tubular housing 3 extends rearward along the direction of the axis O and radially surrounds the outer circumference of a rear end portion 66 of the detection element 6 and the outer circumferences of a separator 8 and a grommet 9 (to be described later), which are disposed rearward of the rear end portion 66.

As shown in FIG. 1, the outer terminal 75 has a tubular forward portion 76 and a rear portion 77 extending rearward in a rodlike form from the forward portion 76. The forward portion 76 is fitted in such a manner that its inner circumferential surface comes into contact with a terminal connection portion 63A (see FIG. 2) to be described later. The forward portion 76 has a slit and can thereby elastically bend in a radial direction, so that contact with the terminal connection portion 63A is maintained with urging force. Thus, electrical connection is ensured between the outer terminal 75 and the detection electrode portion 63. As shown in FIG. 1, similarly, the inner terminal 70 has a tubular forward portion 71 and a rear portion 72 extending in a rodlike form from the forward portion 71. The forward portion 71 is fitted in such a manner that its outer circumferential surface comes into contact with the lead portion 62A. The forward portion 71 has a slit and can thereby elastically bend in a radial direction, so that contact with the lead portion 62A is maintained with urging force. Thus, electrical connection is ensured between the inner terminal 70 and the reference electrode portion 62. The core wires of the lead wires 18 mentioned above are joined to the rear portion 72 of the inner terminal 70 and the rear portion 77 of the outer terminal 75, respectively, through crimping.

As shown in FIG. 1, the tubular separator 8 formed of insulating ceramic is disposed rearward of the rear end portion 66 of the detection element 6 with respect to the direction of the axis O. In order to separate the rear portion 72 of the inner terminal 70 mentioned above, the rear portion 77 of the outer terminal 75 mentioned above, and two electrode terminals 130 (FIG. 1 shows only one electrode terminal 130) to be described later, from one another so as to avoid their mutual contact, the separator 8 has accommodation portions 82 for accommodating them independently of one another. The accommodation portions 82 extend through the separator 8 in the direction of the axis O and are configured to allow aerial communication between the forward side and the rear side with respect to the separator 8. The two lead wires 18 connected to the rear portion 72 of the inner terminal 70 and the rear portion 77 of the outer terminal 75, respectively, extend outward from the oxygen sensor 1 through insertion holes 92 of the grommet 9 to be described later, and are connected to an electronic control unit. Thus, the electronic control unit can apply electricity to the solid electrolyte body 61 through the reference electrode portion 62 and the detection electrode portion 63.

The separator 8 has a flange portion 81 protruding radially outward on its outer circumferential surface. The tubular housing 3 has three or more recesses formed on its outer circumferential surface and disposed along the circumferential direction at a position corresponding to the rear side of the position of disposition of the flange portion 81. The recesses form engagement portions 32 protruding inward within the tubular housing 3. An upward movement of the separator 8 is restricted through the rearward-oriented surface of the flange portion 81 abutting against the engagement portions 32.

Furthermore, a metal holding member 85 is disposed in a gap between the tubular housing 3 and the separator 8 on the forward side of the flange portion 81. The metal holding member 85 is a tubular member made of metal and has a support portion formed by bending its outer end inward. The metal holding member 85 supports the separator 8 through the forward-oriented surface of the flange portion 81 of the separator 8 inserted therethrough being seated on the support portion. In this condition, a portion of the tubular housing 3 corresponding to the disposed metal holding member 85 is crimped from its outer circumferential surface, whereby the metal holding member 85 which supports the separator 8 is fixed to the tubular housing 3.

The grommet 9 is formed of fluororubber and is disposed on the rear side of the separator 8. The grommet 9 is fitted into a rear-end opening 33 of the tubular housing 3 and is held in the tubular housing 3 through crimping of an outer circumference in the vicinity of the opening 33. The grommet 9 has a communication hole 91 extending therethrough in the direction of the axis O for introducing the air into the tubular housing 3. In the oxygen sensor 1, the air is introduced into the tubular housing 3 through the communication hole 91 and the accommodation portions 82 of the separator 8, and the reference electrode 62B within the detection element 6 is thereby exposed to the air. A thin-film-like filter member 87 formed of fluororesin, such as PTFE (polytetrafluoroethylene), and a metal retainer 88 for the filter member 87 are inserted into the communication hole 91, thereby preventing entry of water droplets, etc. Also, the grommet 9 has five insertion holes 92 through which the lead wires 18 and 19 are inserted and which are formed independently of one another (FIG. 1 shows two of the insertion holes 92).

Figure 4:
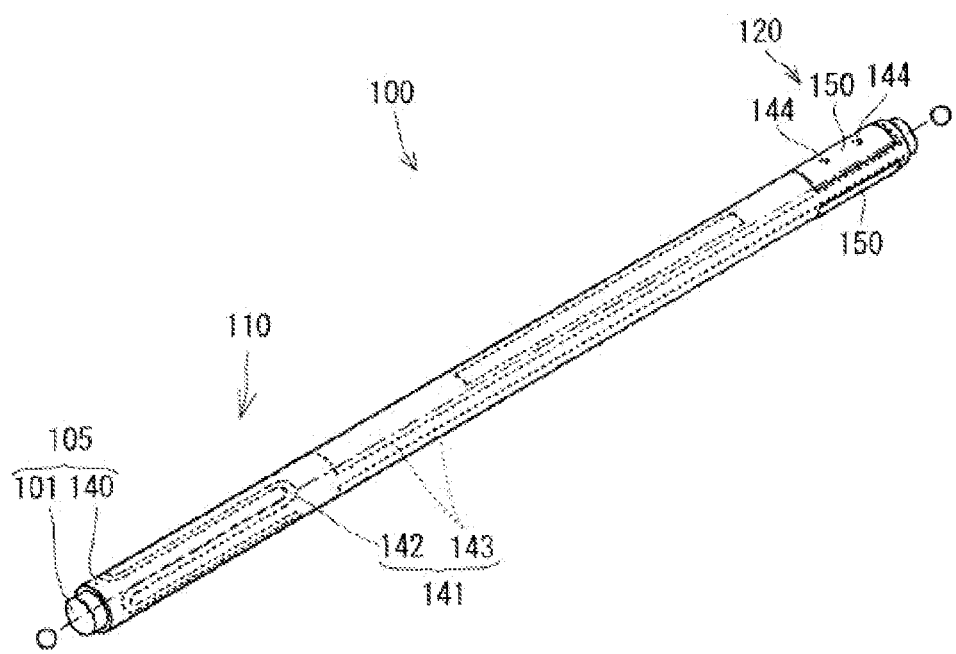
FIG. 4 Perspective view of a heater 100.

Next, with reference to FIGS. 1, 4, and 5, the configuration of the heater 100 will be described. As shown in FIG. 1, the heater 100 for activating the solid electrolyte body 61 through application of heat has a rodlike shape and is inserted into the tubular hole 69 of the detection element 6. A forward end portion 110 of the heater 100 is in contact with the tubular hole 69 (hereinafter, the contact point may be referred to as the point Q). Also, a rear end portion 120 of the heater 100 protrudes from the tubular hole 69 and is disposed within the corresponding accommodation portion 82 of the separator 8. The rear end portion 120 is smaller in outside diameter than the forward end portion 110. In the vicinity of the rear end portion within the tubular hole 69, the outer circumferential surface of the heater 100 is in contact with the inner circumferential surface of the forward portion 71. Also, as shown in FIG. 4, the heater 100 is configured as follows: a rodlike ceramic tube 101 formed of alumina ceramic is used as a core, and the ceramic tube 101 wound with a green sheet 140 formed of alumina ceramic having high insulating performance is fired to form a base body 105. A tungsten-based heat-generating resistor 141 is embedded in the base body 105. The green sheet 140 consists of two sheets, and the heat-generating resistor 141 is formed as a heater pattern between the two sheets and is embedded by firing. The heater pattern of the heat-generating resistor 141 is composed of a heat-generating portion 142 disposed at the forward end portion 110 of the heater 100, and a pair of lead portions 143 connected to the opposite ends of the heat-generating portion 142 and extending toward the rear end portion 120. The pattern of the heat-generating portion 142 is smaller in crosssectional area than the patterns of the lead portions 143 so as to increase electric resistance, and upon application of electricity to the pair of lead portions 143, heat is generated mainly at the heat-generating portion 142.

As shown in FIG. 4, two electrode pads 150 are formed on the outer surface of the rear end portion 120 of the base body 105 of the heater 100. Also, the two lead portions 143 of the heat-generating resistor 141 extend within the green sheet 140 up to the positions of formation of the electrode pads 150, respectively. The green sheet 140 has two through-holes 144 formed side by side in the direction of the axis O at the positions of formation of the two electrode pads 150, respectively. The through-holes 144 are filled with metallization ink. The electrode pads 150 and the lead portions 143 are electrically connected through the through-holes 144.

Furthermore, the electrode terminals 130 (see FIG. 1) are brazed to the two electrode pads 150, respectively. As shown in FIG. 1, the two lead wires 19 are connected to the electrode terminals 130, respectively. Furthermore, the two lead wires 19 extend outward from the oxygen sensor 1 through the tubular holes 92, respectively, of the grommet 9 and are connected to the electronic control unit. Thus, the electronic control unit can apply electricity to the heat-generating portion 142 of the heater 100.

Next, with reference to FIGS. 2, 3, and 5, the configuration and the range of formation of the detection electrode portion 63 will be described. As shown in FIGS. 2 and 3, the detection electrode portion 63 includes the terminal connection portion 63A, a first lead portion 63B, a second lead portion 63C, and a detection electrode 63D. The terminal electrode portion 63A has a ring-like shape and is provided on the outer circumferential surface 61A at a rear end portion of the solid electrolyte body 61 via an insulating member (not shown) along the circumferential direction. The terminal connection portion 63A is in contact with the forward portion 76 of the outer terminal 75 (see FIG. 1) and is thereby electrically connected to the outer terminal 75.

The first lead portion 63B having a fixed circumferential length; i.e., a predetermined width, and extending vertically from a portion of the forward end edge of the terminal connection portion 63A toward the forward end of the detection element 6 is provided on the outer circumferential surface 61A via the insulating member (not shown). The first lead portion 63B extends up to a position located slightly forward of the diameter-expanded portion 67. As shown in FIG. 2, when the first lead portion 63B is viewed from the front side, the vertically extending centerline of the first lead portion 63B passes through the point Q mentioned above. Also, as shown in FIG. 3, the first lead portion 63B is provided only on the front side of the outer circumferential surface 61A. The first lead portion 63B and the terminal connection portion 63A are electrically connected to each other through contact.

The second lead portion 63C having the same circumferential length as that of the first lead portion 63B and extending vertically from the forward end of the first lead portion 63B toward the forward end of the detection element 6 is provided on the outer circumferential surface 61A via the insulating member (not shown). The second lead portion 63C extends to a forward end portion of the detection portion 64. As shown in FIG. 2, when the second lead portion 63C is viewed from the front side, similar to the first lead portion 63B, the vertically extending centerline of the second lead portion 63C passes through the point Q. Also, as shown in FIG. 3, the second lead portion 63C is provided only on the front side of the outer circumferential surface 61A. The second lead portion 63C and the first lead portion 63B are electrically connected to each other through contact.

As shown in FIG. 2, the detection electrode 63D having a circumferential length longer than that of the second lead portion 63C and extending vertically from the forward end of the second lead portion 63C to the forward end of the detection element 6 is provided on the outer circumferential surface 61A. The detection electrode 63D linearly extends from the forward end of the second lead portion 63C and is provided in such a manner as to cover a spherically closed forward end portion of the detection element 6. As shown in FIG. 3, the detection electrode 63D is provided only on the front side of the outer circumferential surface 61A. Furthermore, as shown in FIG. 2, when the detection electrode 63D is viewed from the front side, similar to the second lead portion 63C, the vertically extending centerline of the detection electrode 63D passes through the point Q. The detection electrode 63D and the second lead portion 63C are electrically connected to each other through contact.

As shown in FIG. 3, the detection electrode 63D is partially formed at the forward side of the detection portion 64. Specifically, a surface area S of the detection electrode 63D is 8% to 20%, more preferably 14%, of a surface area T of the detection portion 64. Through employment of this relation, the range of formation of the detection electrode 63D is limited to the vicinity of the point Q. Therefore, as will be described later, when the electronic control unit applies electricity to the solid electrolyte body 61 for performing temperature control of the solid electrolyte body 61, current which flows reflects only the temperature of a most activated region in the vicinity of the point Q. As a result, the electronic control unit can perform accurate temperature control.

In the case where S is less than 8% of T, since the amount of formation of the detection electrode 63D is small, at the time of heating by the heater 100, the detection electrode 63D is apt to be consumed through sublimation. Thus, the oxygen sensor 1 deteriorates in durability against a high temperature.

Also, in the case where S is in excess of 20% of T, the detection electrode 63D also covers a region of the solid electrolyte body 61 other than the vicinity of the point Q. Thus, in temperature control of the solid electrolyte body 61, even though the electronic control unit applies electricity to the solid electrolyte body 61 as will be described later, the electronic control unit fails to perform temperature control with high accuracy. More specifically, current which flows in the solid electrolyte body 61 involves an error corresponding to a difference in temperature between a most activated region of the solid electrolyte body 61 in the vicinity of the point Q and the other region; thus, the electronic control unit cannot accurately detect the temperature of the solid electrolyte body 61 and thereby fails to perform highly accurate temperature control on the solid electrolyte body 61.

Figure 15:
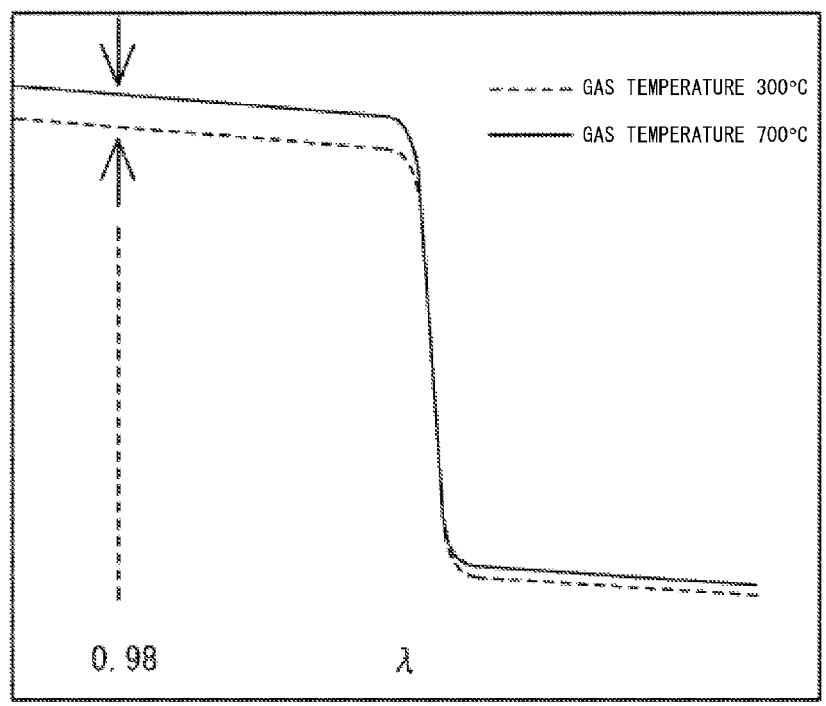
FIG. 15 Graph showing the conditions of a test for variations of output of the oxygen sensor 1.

With reference to FIGS. 15 and 16, there will be described the results of a test for variations of output of the oxygen sensor 1 conducted on test samples having a conventional S/T ratio, an S/T ratio of 50%, an S/T ratio of 20%, an S/T ratio of 10%, and an S/T ratio of 5%. This test compared variations of the output voltage (mV) of the oxygen sensor 1 at a $\lambda$ of 0.98 when the temperature of exhaust gas was varied in a range of 300° C. to 700° C. as shown in FIG. 15 with the internal resistance of the detection element 6 held at a fixed value. $\lambda$ is a coefficient indicative of a difference between the theoretical amount of air and an actually supplied amount of air. As is apparent from FIG. 16, at an S/T ratio equal to or less than 20%; i.e., an S/T ratio of 20%, 10%, and 5%, variations of the output voltage (mV) of the oxygen sensor 1 were greatly improved as compared with those of the conventional oxygen sensor. Therefore, the S/T ratio is desirably 20% or less.

Next, with reference to FIGS. 17 and 18, the results of a durability test on the oxygen sensor 1 will be described. As shown in FIG. 17, this test was conducted by use of an actual engine and employed an operation pattern consisting of a 50-minute run with an exhaust gas temperature of 900° C. to 950° C. and a subsequent 10-minute idling operation. This operation pattern was repeated for 1,000 hours, 2,000 hours, and 3,000 hours. FIG. 18 shows the results of this durability test. The results of the durability test shown in FIG. 18 are the results of observation on deterioration of electrodes through an electron microscope after the deterioration test. "Poor" indicates that the electrodes deteriorated through sublimation, and "Good" indicates that the electrodes were free from deterioration through sublimation. In the case of an S/T ratio of 5%, the following has been found: in the 1,000-hour and 2,000-hour runs, since the amount of formation of the detection electrodes 63D is small, the detection electrodes 63D are consumed through sublimation. In the case of an S/T ratio of 8%, in the 1,000-hour, 2,000-hour, and 3,000-hour runs, the detection electrodes 63D were free from consumption through sublimation. Similarly, in the case of an S/T ratio of 50%, in the 1,000-hour, 2,000-hour, and 3,000-hour runs, the detection electrodes 63D were free from consumption through sublimation. Therefore, in the case of an S/T ratio of less than 8%, the following has been found: the amount of formation of the detection electrode 63D is small; as a result, the oxygen sensor 1 deteriorates in durability against a high temperature. Thus, the S/T ratio is desirably 8% to 20%.

Figure 5:
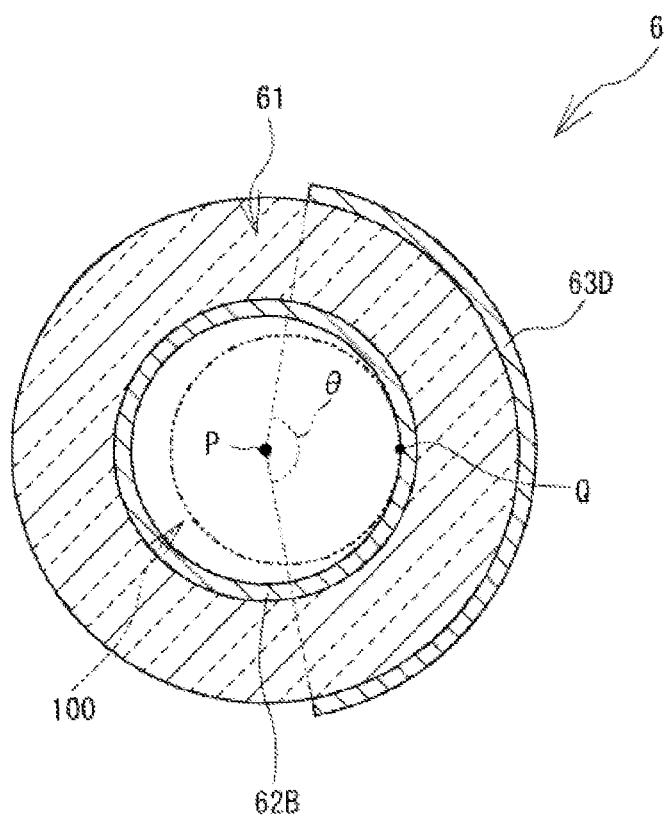
FIG. 5 Sectional view of the detection element 6 taken along the dot-dash line A-A of FIG. 2 and viewed from the direction of the arrows.
Figure 14:
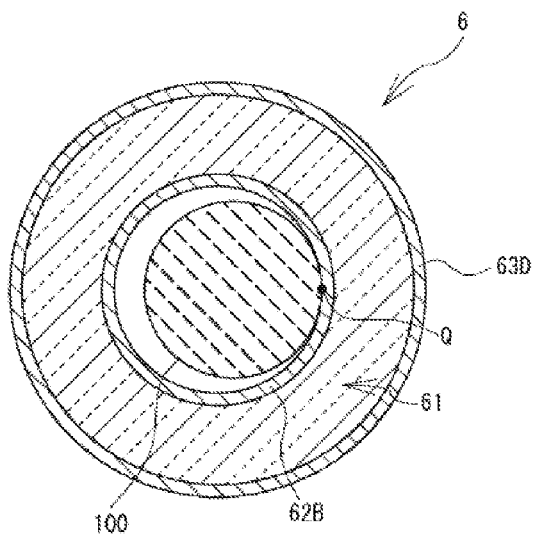
FIG. 14 Sectional view of a conventional detection element 6 having a reference electrode 62B and a detection electrode 63D taken along a plane in parallel with its radial direction.

As shown in FIG. 5, of angles formed by a line segment connecting one circumferential end of the detection electrode 63D and a center P of the solid electrolyte body 61 and a line segment connecting the other circumferential end of the detection electrode 63D and the center P, an angle θ in a region which contains the detection electrode 63D is less than 180°, more preferably 160°. As will be described later, through employment of an angle θ of less than 180°, in a plating process for forming the detection electrode 63D on the detection element 6, a mask 170 can be attached to the solid electrolyte body 61 with sufficient gripping force. Thus, when the detection element 6 is immersed in a plating solution, there can be prevented entry of the plating solution between the inner circumferential surface of the mask 170 and the outer circumferential surface 61A of the solid electrolyte body 61. In the case of an angle θ equal to or greater than 180°, the gripping force of the mask 170 is insufficient, so that the plating solution enters between the inner circumferential surface of the mask 170 and the outer circumferential surface 61A. For convenience of visibility of drawing, the thicknesses of the reference electrode 62B and the detection electrode 63D shown in FIG. 5 are exaggeratingly shown, and the same also applies to FIG. 14.

Furthermore, as shown in FIG. 2, with respect to the vertical direction, a length X of the detection electrode 63D is 40% or less, more preferably 36%, of a length Y of the detection portion 64. By virtue of X being 40% or less of Y, the detection electrode 63D is provided on the outer circumferential surface 61A in such a manner as to cover the vicinity of the point Q and the heat-generating portion 142 of the heater 100 in the vicinity of the point Q. At the time of heating by the heater 100, a region of the solid electrolyte body 61 in the vicinity of the point Q is most activated through generation of heat of the heat-generating portion 142. Therefore, the electronic control unit can reliably detect the temperature of the solid electrolyte body 61 at a most activated region. In the case where X is greater than 40% of Y, the electronic control unit may detect the temperature of a region other than the vicinity of the point Q and thereby fails to accurately perform temperature control of the solid electrolyte body 61.

Next, with reference to FIGS. 19 and 20, there will be described the results of a test for variations of temperature of the detection element 6 of the oxygen sensor 1 conducted on test samples having an X/Y ratio of 100%, 50%, 40%, and 20%, where X is the length of the detection electrode 63D, and Y is the length of the detection portion 64. In this test, as shown in FIG. 19, while the temperature of exhaust gas was varied in a range of 300° C. to 700° C. with the internal resistance of the detection element 6 held at a fixed value, the temperature of the detection element 6 was measured by use of a thermocouple 10. As shown in FIG. 20, as compared with the oxygen sensors 1 having an X/Y ratio of 100% and 50%, the oxygen sensors 1 having an X/Y ratio of 40% and 20% exhibited a great improvement with respect to variations of temperature of the detection element 6. Therefore, the X/Y ratio is desirably 40% or less.

Figure 6:
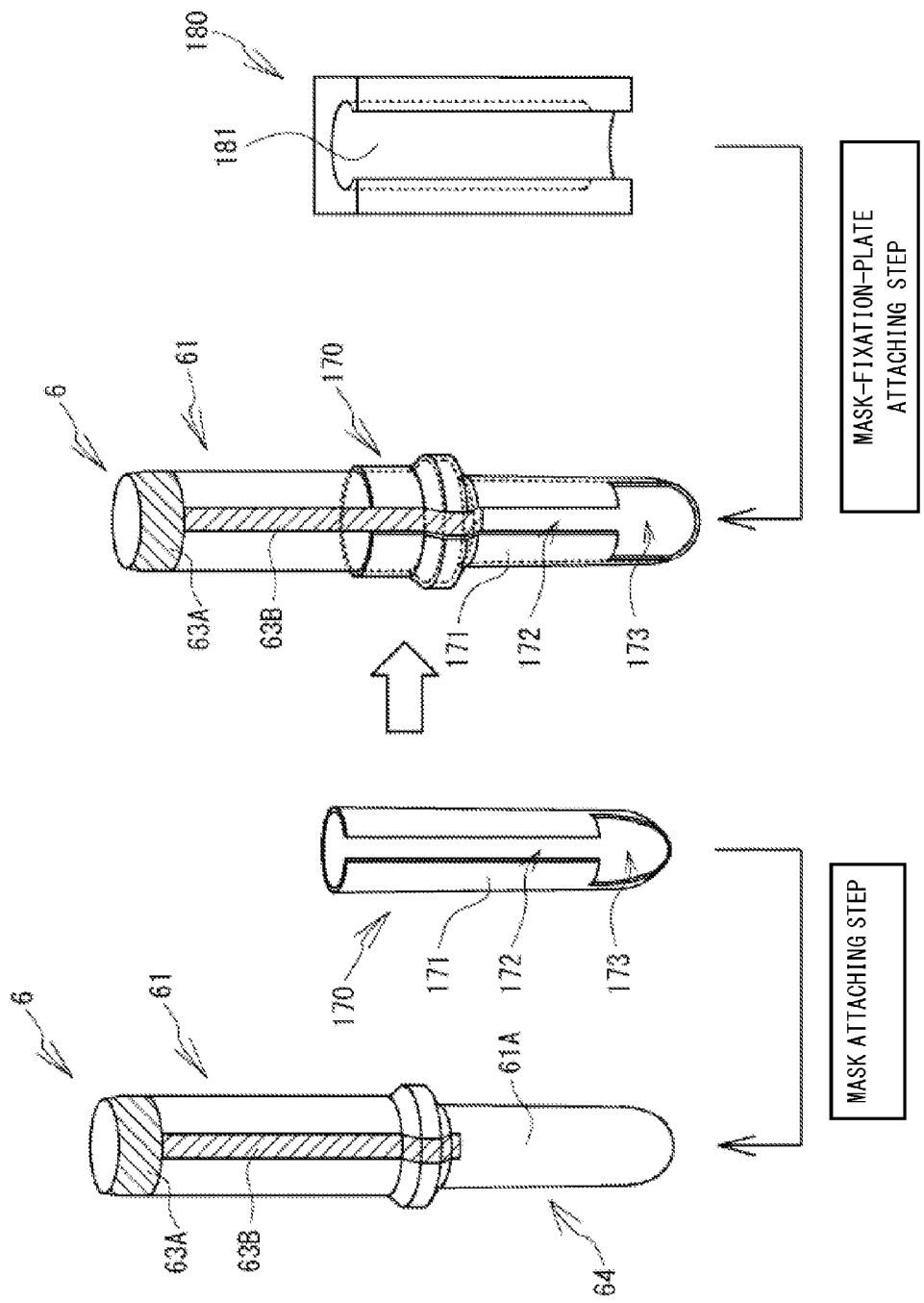
FIG. 6 View showing the steps of attaching a mask 170 and a mask fixation plate 180 in a plating process for the detection element 6.
Figure 7:
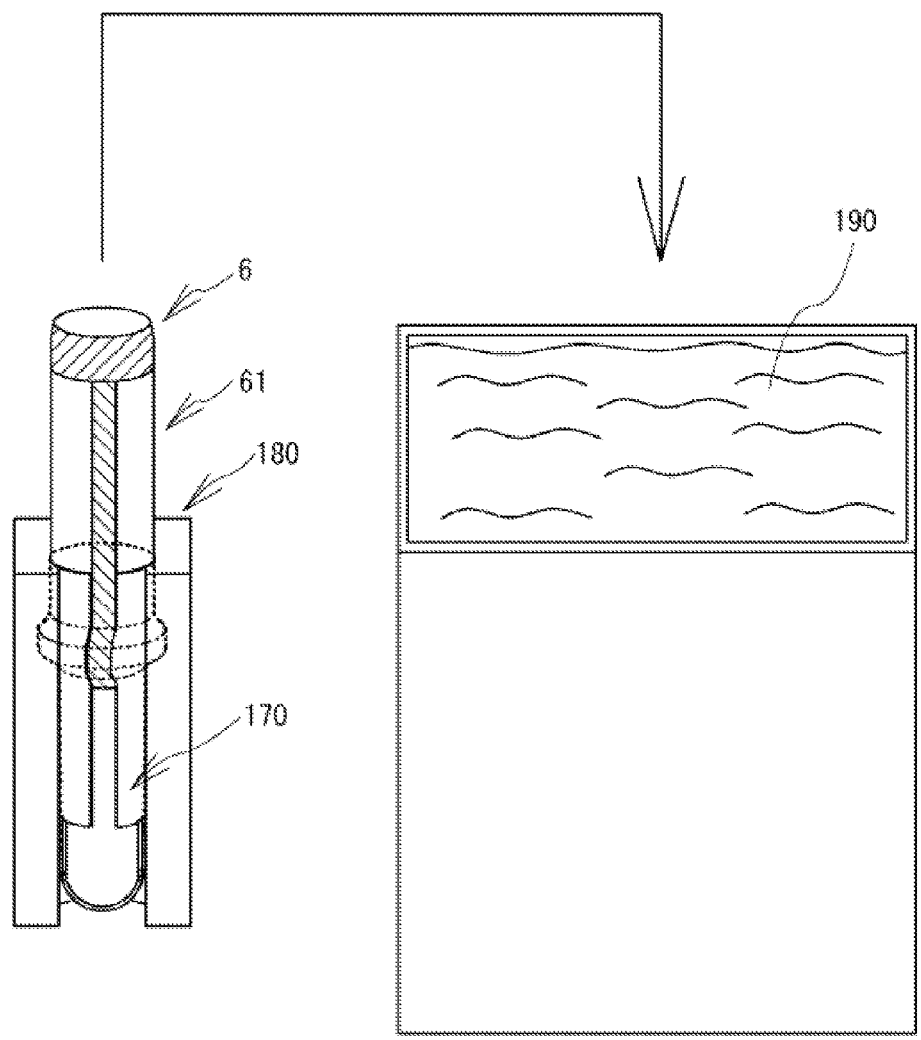
FIG. 7 View showing a step of immersing the detection element 6 in a plating solution 190 in the plating process.

Next, there will be described a plating process for forming the second lead portion 63C and the detection electrode 63D on the detection element 6. As shown in FIGS. 6 and 7, the plating process uses the mask 170 for masking the detection element 6, a mask fixation plate 180 for fixing the solid electrolyte body 61 attached with the mask 170, and a plating solution 190. The terminal connection portion 63A and the first lead portion 63B are formed beforehand on the outer circumferential surface 61A by a printing process. In the following description, the left side, the right side, the upper side (rear side), the lower side (forward side), the front side, and the far side which are already defined for the detection element 6 are similarly defined as the left side, the right side, the upper side (rear side), the lower side (forward side), the front side, and the far side for the mask 170 and the mask fixation plate 180 shown in FIG. 6.

Figure 8:
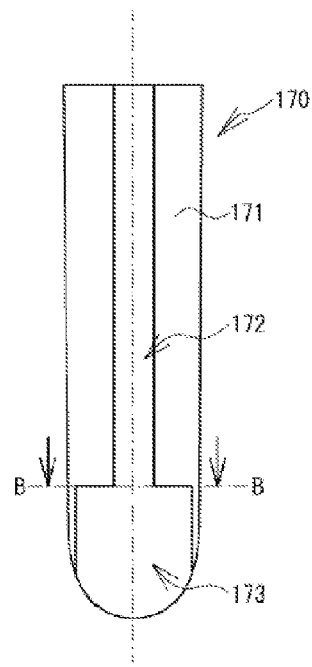
FIG. 8 Front view of the mask 170.
Figure 9:
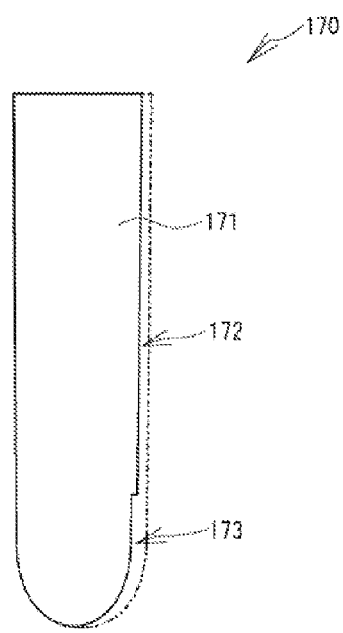
FIG. 9 Left side view of the mask 170.

As shown in FIG. 6, the mask 170 has a substantially tubular shape having a closed forward end. The mask 170 is formed of an elastic rubber member, and its tubular hole has an inside diameter smaller than the outside diameter of the detection portion 64 of the solid electrolyte body 61. Thus, when the mask 170 is attached to the solid electrolyte body 61, the inner circumferential surface of the mask 170 and the outer circumferential surface 61A of the solid electrolyte body 61 can be in close contact with each other along the vertical direction. As shown in FIG. 8, the mask 170 has a first slit 172 and a second slit 173 on its outer circumferential surface 171. The first slit 172 extends forward from the rear end of the mask 170 in the vertical direction with a fixed width. As shown in FIG. 9, the first slit 172 is provided on the outer circumferential surface 171 only on the front side. As shown in FIG. 6, when the mask 170 is attached to the solid electrolyte body 61, the first slit 172 exposes a region of the outer circumferential surface 61A where the first lead portion 63B is formed, and a region where the second lead portion 63C is to be formed.

As shown in FIG. 8, the second slit 173 longer in circumferential length on the outer circumferential surface 171 than the first slit 172 extends in the vertical direction from the forward end of the first slit 172 and to the forward end of the mask 170. As shown in FIG. 8, when the mask 170 is viewed from the front side, the vertically extending centerline of the first slit 172 and the vertically extending centerline of the second slit 173 coincide with each other. Also, as shown in FIG. 9, the second slit 173 is provided on the outer circumferential surface only on the front side. When the mask 170 is attached to the solid electrolyte body 61, the second slit 173 exposes a region of the outer circumferential surface 61A where the second lead portion 63C is to be formed.

Figure 10:
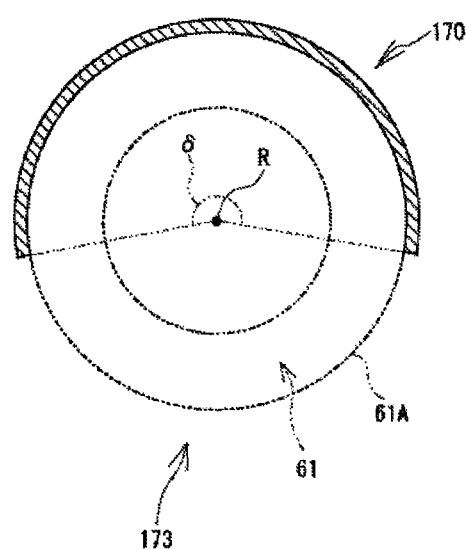
FIG. 10 Sectional view of the mask 170 taken along the dot-dash line B-B of FIG. 8 and viewed from the direction of the arrows.

As mentioned above, the circumferential range of formation of the detection electrode 63D on the outer circumferential surface 61A is half or less of the outer circumferential surface 61A (see FIG. 2). Thus, as shown in FIG. 10, of angles formed by a line segment connecting a center R of the mask 170 and one circumferential end of the second slit 173 and a line segment connecting the center R and the other end of the second slit 173, an angle δ in a region which does not contain the second slit 173 is 180° or greater. Accordingly, the mask 170 is attached to the solid electrolyte body 61 with sufficient gripping force. Therefore, when the solid electrolyte body 61 attached with the mask 170 is immersed in the plating solution 190 to be described later, the plating solution 190 does not enter between the inner circumferential surface of the mask 170 and the outer circumferential surface 61A of the solid electrolyte body 61. The present embodiment employs an angle δ of 200° by way of example. Also, since the first slit 172 shorter in circumferential length on the outer circumferential surface 171 than the second slit 173 can provide a gripping force greater than that provided by the second slit 173, entry of the plating solution 190 can be similarly prevented.

As shown in FIG. 6, the mask fixation plate 180 formed of an elastic rubber member has a substantially rectangular parallelepiped shape having a through-hole 181. The through-hole 181 is circular as viewed in plane and extends vertically through the mask fixation plate 180. Thus, the mask fixation plate 180 opens at the front side along the vertical direction. The inside diameter of the through-hole 181 is smaller than the outside diameter of a rear end portion of the detection portion 64 of the solid electrolyte body 61. Accordingly, upon attachment to the solid electrolyte body 61 attached with the mask 170, the mask fixation plate 180 can unitarily fix the solid electrolyte body 61 and the mask 170.

Next, there will be described a process for forming the second lead portion 63C and the detection electrode 63D on the detection element 6 by a plating process. As shown in FIG. 6, in a "mask attaching step," the mask 170 is attached to the solid electrolyte body 61 on which the terminal connection portion 63A and the first lead portion 63B are formed beforehand by a printing process. At this time, the mask 170 is attached to the solid electrolyte body 61 while positioning such that the vertically extending centerlines of the first lead portion 63B and the first slit 172 coincide with each other as viewed from the front side and such that the forward end positions of the solid electrolyte body 61 and the mask 170 coincide with each other. A nucleating process is performed beforehand in a region to be subjected to the plating process. As shown in FIG. 6, in a "mask-fixation-plate attaching step," the mask fixation plate 180 is attached to the solid electrolyte body 61 attached with the mask 170. At this time, the attachment is performed while positioning such that the vertically extending centerline of the first lead portion 63B and the axis of the through-hole 181 coincide with each other as viewed from the front side and such that the forward end of the solid electrolyte body 61 and the forward end of the mask fixation plate 180 coincide with each other. Furthermore, as shown in FIG. 7, the solid electrolyte body 61 attached with the mask 170 and the mask fixation plate 180 are immersed in the plating solution 190 contained in a predetermined container. As a result of the solid electrolyte body 61 being immersed in the plating solution, the plating process is performed only in a region of the outer circumferential surface 61A which is exposed from the first slit 172 and the second slit 173 and has undergone the nucleating process. Thus, the second lead portion 63C and the detection electrode 63D are formed on the outer circumferential surface 61A.

FIG. 21 shows the results of the plating process for forming the detection electrode 63D on the detection element 6 while the shape of the mask 170 was varied such that the angle θ in the region which contained the detection electrode 63D as shown in FIG. 5 had 50°, 100°, 160°, and 180°. As shown in FIG. 21, at an angle θ of 50° to 160°, plating blur did not arise. By contrast, at an angle θ of 180°, plating blur arose. Therefore, the angle θ is desirably less than 180°.

Next, temperature control of the solid electrolyte body 61 will be described. In the course of use of the oxygen sensor 1, in order to maintain the solid electrolyte body 61 activated through application of heat by the heater 100 at a fixed temperature, the electronic control unit (not shown) performs temperature control of the solid electrolyte body 61. Specifically, the electronic control unit mentioned above applies current to the solid electrolyte body 61 intervening between the reference electrode portion 62 and the detection electrode portion 63 through the pair of lead wires 18. On the basis of current which flows as a result of application of electricity, the electronic control unit reads the resistance of the solid electrolyte body 61 and detects the temperature of the solid electrolyte body 61 on the basis of the read resistance. On the basis of a difference between the detected temperature and an intended temperature of the solid electrolyte body 61, the electronic control unit controls application of electricity to the lead portions 143 through the pair of lead wires 19. Through this control, the electronic control unit adjusts the magnitude of heat generation of the heat-generating portion 142 of the heater 100, thereby adjusting heating of the solid electrolyte body 61 by the heater 100. As a result, the solid electrolyte body 61 assumes the intended temperature and subsequently maintains the intended temperature. Thus, output of the detection element 6 is maintained constant.

As described above, in the oxygen sensor 1 of the present embodiment, the detection electrode 63D is formed on the outer circumferential surface 61A only in the vicinity of a region which faces, across the solid electrolyte body 61, the point Q where the forward end portion 110 of the heater 100 is in contact with the reference electrode portion 62. Additionally, the surface area S of the detection electrode 63D is 8% to 20% of the surface area T of the detection portion 64. That is, the range of formation of the detection electrode 63D is limited to the vicinity of the point Q and to a predetermined range. Through limitation on the range of formation, the detection element 6 can provide output outward without being influenced by an inactive region of the solid electrolyte body 61.

Also, current which flows when the solid electrolyte body 61 is energized and activated reflects only the resistance of a most activated region of the solid electrolyte body 61 in the vicinity of the point Q. As a result, the electronic control unit can perform control on the basis of only the temperature of a most activated region of the solid electrolyte body 61 such that the solid electrolyte body 61 assumes an intended temperature. Thus, even when the temperature of the solid electrolyte body 61 differs from region to region, the electronic control unit can accurately performs temperature control of the solid electrolyte body 61, so that output of the detection element 6 is constant. That is, irrespective of temperature of gas to be measured, the electronic control unit can accurately control the temperature of the solid electrolyte body 61, so that the response performance of the detection element 6 can be improved.

Also, by virtue of an S/T ratio of 8% or more, even when the detection electrode 63D assumes a high temperature as a result of heating by the heater 100, the detection electrode 63D can be resistant to consumption through sublimation, so that the oxygen sensor 1 can achieve durability against a high temperature. Furthermore, through employment of an S/T ratio of 20% or less, the detection electrode 63D is disposed only in the vicinity of the point Q. Thus, when the heater 100 generates heat, the solid electrolyte body 61 easily increases in temperature. Thus, the oxygen sensor 1 can achieve good response performance. Also, by virtue of an S/T ratio of 20% or less, there can be reduced the amount of use of material, such as platinum or a platinum alloy, for forming the detection electrode 63D, so that the cost of the oxygen sensor 1 can be reduced.

Also, the circumferential range of formation of the detection electrode 63D on the outer circumferential surface 61A of the solid electrolyte body 61 is equal to or less than half of the outer circumferential surface 61A. Thus, in the plating process for forming the detection electrode 63D, the mask 170 to be attached to the solid electrolyte body 61 before immersion in the plating solution 190 can cover half or more of the outer circumferential surface 61A. Therefore, the mask 170 can be attached to the solid electrolyte body 61 with sufficient gripping force. That is, when the detection element 6 is immersed in the plating solution 190, there can be prevented entry of the plating solution between the outer circumferential surface 61A and the inner circumferential surface of the mask 170.

Also, the detection electrode 63D is formed on the outer circumferential surface 61A at an X/Y ratio of 40% or less. Thus, the detection electrode 63D is reliably provided in the vicinity of the point Q where the solid electrolyte body 61 assumes a highest temperature at the time of activation, and in the vicinity of the heat-generating portion 142 of the heater 100. Accordingly, current which reflects a highest temperature of the solid electrolyte body 61 reliably flows in the detection electrode 63D. Therefore, regardless of whether or not the temperature of the activated solid electrolyte body 61 differs from region to region; i.e., regardless of the temperature of gas to be detected, the electronic control unit reliably detects a highest temperature of the solid electrolyte body 61 and can thereby accurately perform temperature control of the solid electrolyte body 61.

Figure 22:
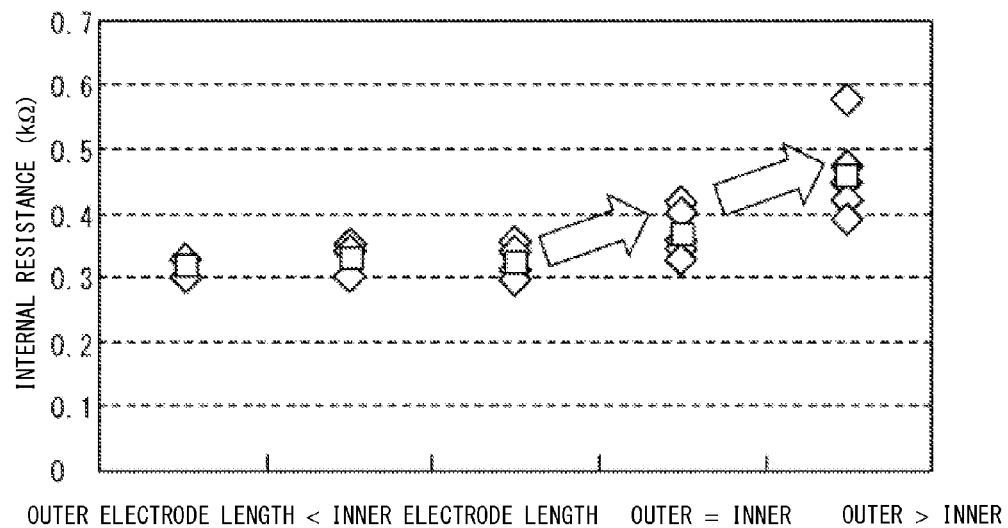
FIG. 22 Views showing the relationship between the internal resistance of the detection element 6 and the positional relation between an outer electrode portion and an inner electrode portion at a temperature of the detection element 6 of 600° C.
Figure 22:
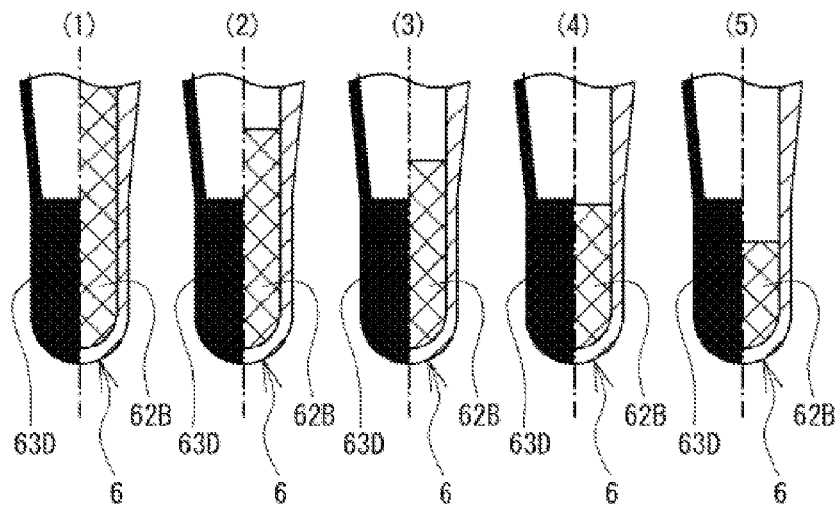

Next, with reference to FIG. 22, there will be described the relation of the internal resistance of the detection element 6 with the length of the detection electrode 63D, which is an outer electrode portion, along the axial direction of the detection element 6 and the length of the reference electrode 62B, which is an inner electrode portion, along the axial direction of the detection element 6. The drawings shown in FIG. 22 show the relationship between the internal resistance of the detection element 6 and the positional relation between the outer electrode portion and the inner electrode portion at a temperature of the detection element 6 of 600° C. As shown in (1) to (3) in FIG. 22, in the case where, with respect to the direction of the axis of the detection element 6, the length of the inner electrode portion (the reference electrode 62B) is longer than the length of the outer electrode portion (the detection electrode 63D), variations of internal resistance of the detection element 6 are small; i.e., the internal resistance is stable. By contrast, in the case where the length of the outer electrode portion (the detection electrode 63D) is equal to the length of the inner electrode portion (the reference electrode 62B) or where the length of the outer electrode portion (the detection electrode 63D) is longer than the length of the inner electrode portion (the reference electrode 62B), variations of internal resistance of the detection element 6 are large. Therefore, the length of the inner electrode portion (the reference electrode 62B) is desirably longer than the length of the outer electrode portion (the detection electrode 63D). That is, with respect to the direction of the axis of the detection element 6, the rear end of the inner electrode portion (the reference electrode 62B) is desirably located rearward of the rear end of the outer electrode portion (the detection electrode 63D). In this case, variations of internal resistance of the detection element 6 are small; i.e., the internal resistance is stable.

Figure 11:
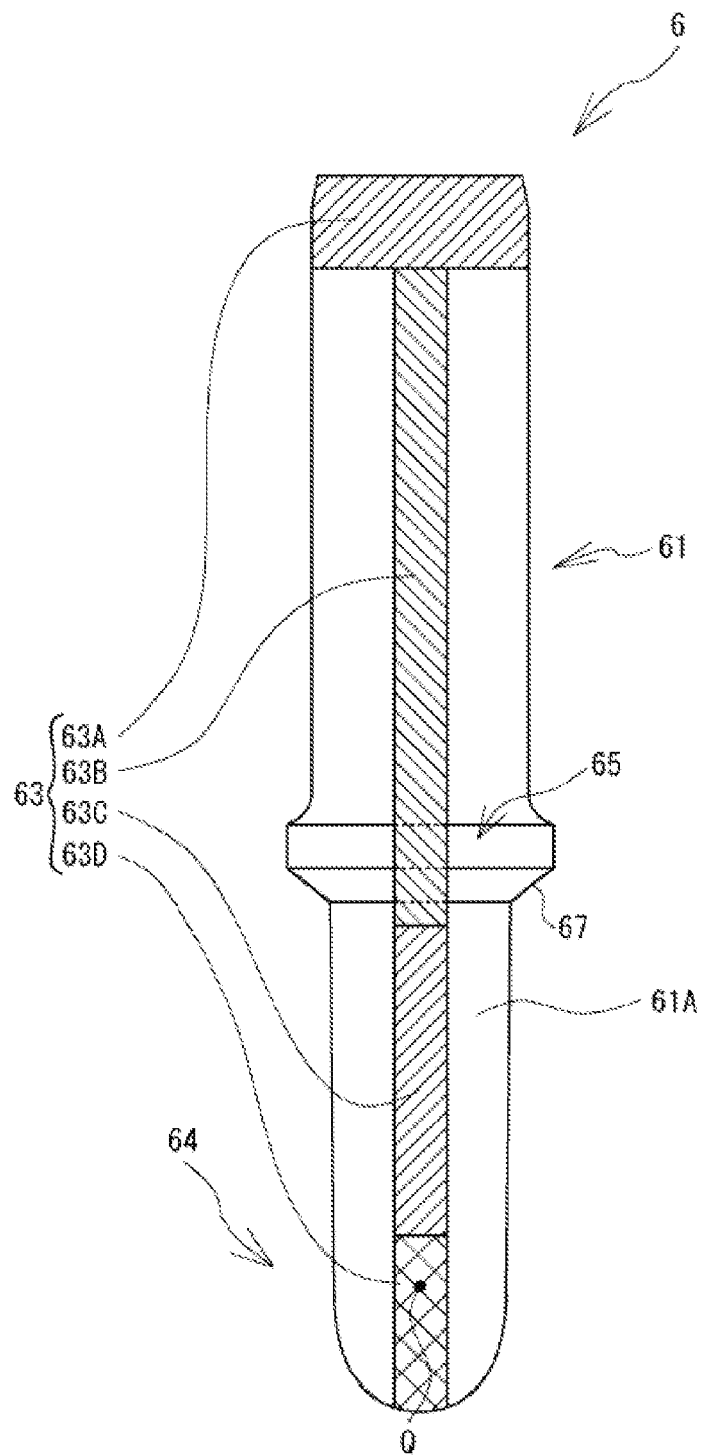
FIG. 11 Front view of the detection element 6 in a first modification.
Figure 12:
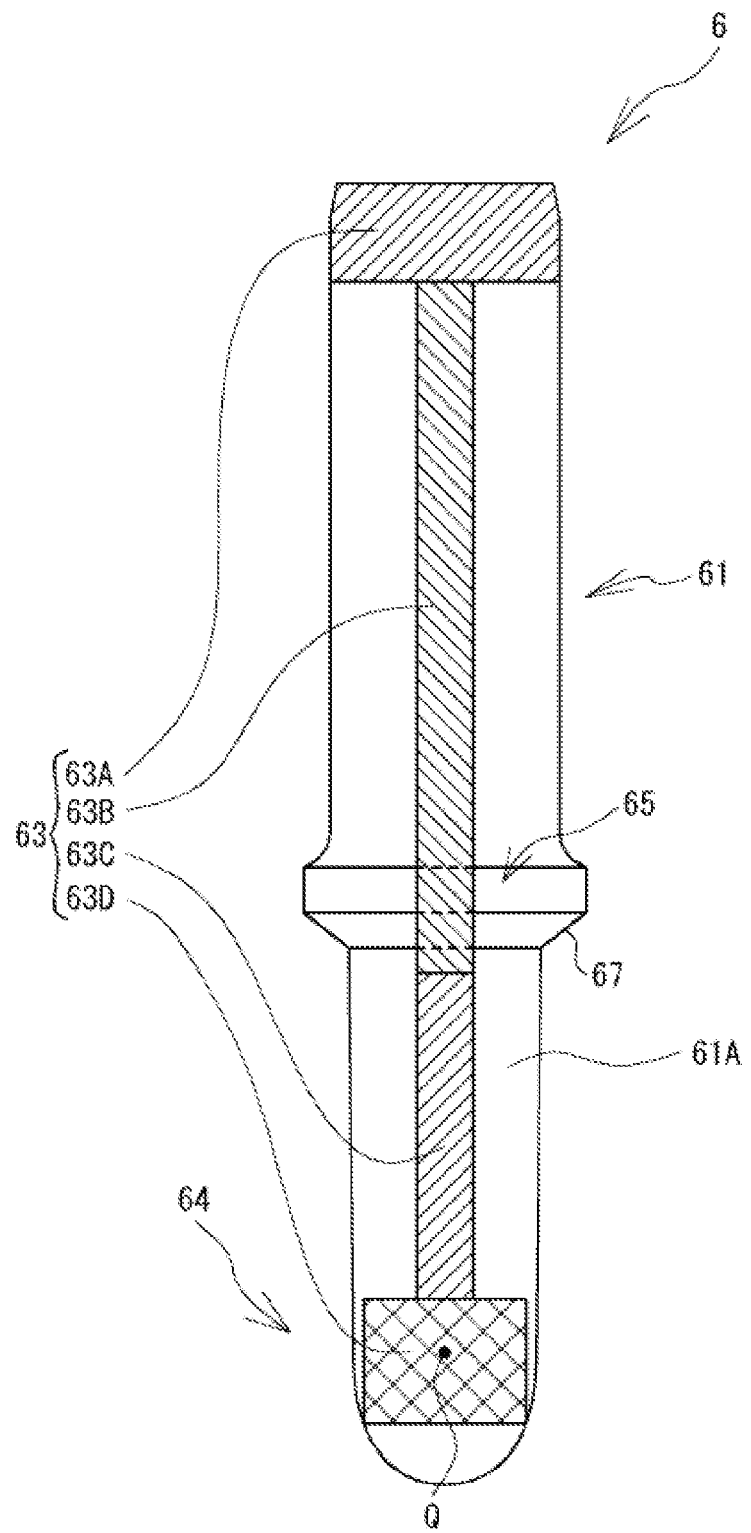
FIG. 12 Front view of the detection element 6 in a second modification.
Figure 13:
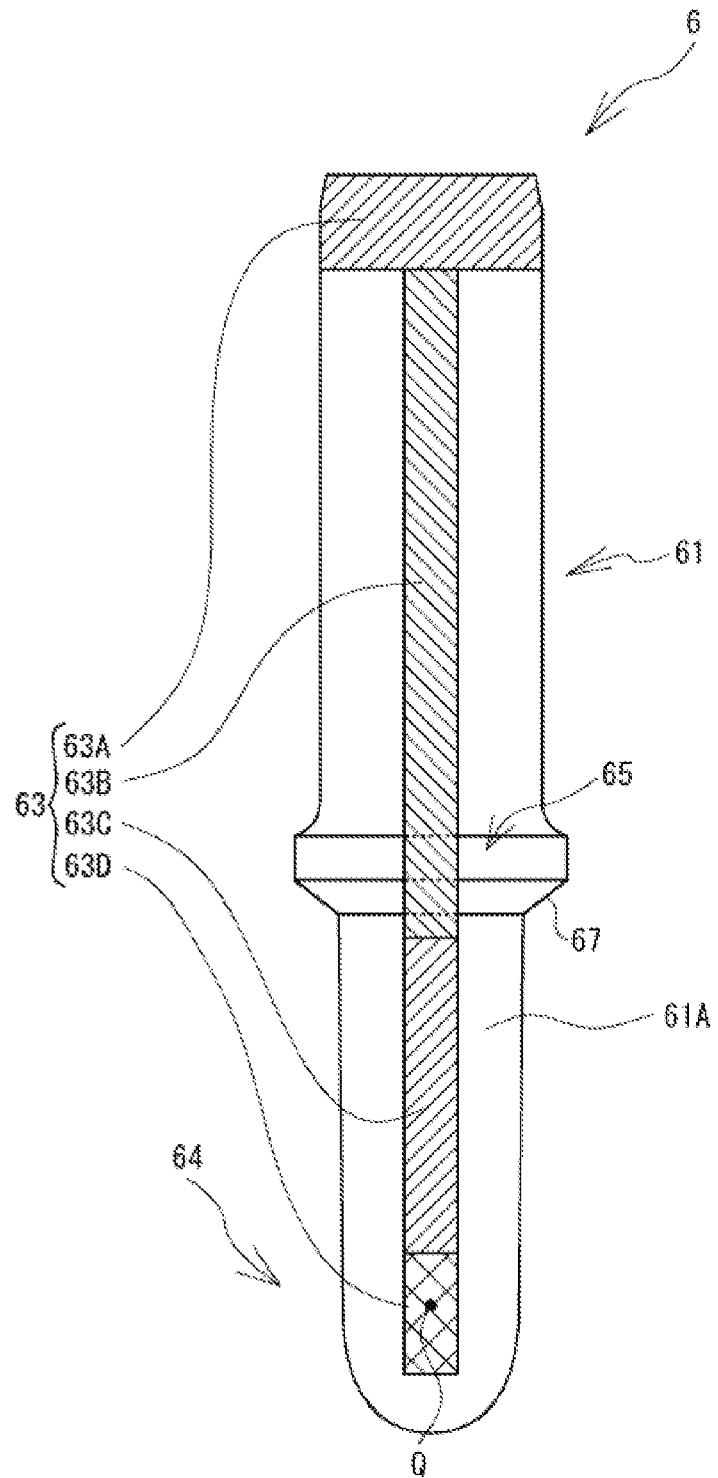
FIG. 13 Front view of the detection element 6 in a third modification.

The present invention is not limited to the above-described embodiment, but may be modified in various other forms. For example, as shown in FIG. 11, the circumferential length of the detection electrode 63D on the outer circumferential surface 61A may be substantially equal to that of the second lead portion 63C. In this case, further limitation is imposed on the detection electrode 63D. As a result, current which flows in the detection electrode 63D at the time of application of electricity can more reliably reflects a highest temperature of the solid electrolyte body 61, so that the electronic control unit can accurately perform temperature control of the solid electrolyte body 61. Also, as shown in FIGS. 12 and 13, the detection electrode 63D may not be formed at a spherically closed forward end portion of the detection portion 64 so long as the detection electrode 63D is provided in the vicinity of the point Q. In this case, the cost of the oxygen sensor 1 can be further reduced. As shown in FIGS. 11 and 13, in the case where the detection electrode 63D and the second lead portion 63C have the same circumferential length, a distinction between the detection electrode 63D and the second lead portion 63C is such that a portion located forward of the rear end of the heat-generating portion 142 of the heater 100 is the detection electrode 63D, whereas a portion located rearward of the rear end is the second lead portion 63C.

Also, the reference electrode 62B, which is the inner electrode portion, may have at least an inner partial electrode portion formed partially with respect to the circumferential direction of the inner surface of the detection element 6, and the inner partial electrode portion may be disposed at such a position as to face at least partially the detection electrode 63D, which is the outer partial electrode portion, with the solid electrolyte body 61 intervening therebetween. In this case, the inner partial electrode portion and the outer partial electrode portion are disposed in such a mutually facing manner as to face each other at least partially, and the heater is in contact with its vicinity; therefore, element activating time can be shortened. Also, the heater 100 may be in contact with an inner side surface of the inner surface of the sensor element 6.

Also, the present invention is not limited to an oxygen sensor for detecting exhaust gas exhausted from an engine as in the case of the embodiment described above, but is applicable to gas sensors for detecting various gases to be detected. Also, the present invention is applicable to a gas sensor to be attached to a suction pipe of the engine. Furthermore, the detection electrode 63D may not have a rectangular shape as viewed from the front side as shown in FIG. 12, but may have a curved shape, such as an elliptic shape, whose longitudinal direction coincides with the vertical direction. Also, the present invention is not limited to the mode in which the heater 100 is in contact with only the inner side surface of the detection element 6 as shown in FIG. 1, but is also applicable to, for example, a mode in which the heater 100 is in contact with a bottom portion of the detection element 6.

In the present embodiment, the oxygen sensor 1 corresponds to the "gas sensor;" the detection element 6 corresponds to the "sensor element;" the outer circumferential surface 61A corresponds to the "outer surface;" the reference electrode 62B corresponds to the "inner electrode portion;" the detection electrode 63D corresponds to the "outer electrode portion;" the lead portion 62A, the first lead portion 63B, and the second lead portion 63C collectively correspond to the "lead portion;" the detection portion 64 corresponds to the "gas contact portion;" the tubular hole 69 corresponds to the "inner surface;" the axis O corresponds to the "axis;" the center P corresponds to the "center;" the point Q corresponds to the "contact portion;" and the angle θ corresponds to the "angle."

DESCRIPTION OF REFERENCE NUMERALS

1: oxygen sensor
6: detection element
61: solid electrolyte body
61A: outer circumferential surface
62A: lead portion
62B: reference electrode
63B: first lead portion
63C: second lead portion
63D: detection electrode
64: detection portion
69: tubular hole
100: heater
141: heat-generating resistor
142: heat-generating portion
O: axis
P: center
Q: point
S, T: surface area
X, Y: length
θ: angle

The invention claimed is:

1. A gas sensor to be exposed to gas to be measured, comprising
a sensor element having
a closed-bottomed tubular solid electrolyte body having a closed forward end and extending in a direction of an axis,
an outer electrode portion provided on an outer surface of a forward end portion of the solid electrolyte body, and
an outer lead portion extending rearward from the outer electrode portion in the direction of the axis and having a circumferential width narrower than a width of a rear end region of the outer electrode portion; and
a heater having a heat-generating portion formed of a heat-generating resistor which generates heat through application of electricity, and being in contact with an inner surface of the sensor element,
the gas sensor being characterized in that
the outer electrode portion has at least an outer partial electrode portion formed partially with respect to a circumferential direction of the outer surface, and the outer electrode portion is disposed at such a position as to face a contact portion of the inner surface of the sensor element in contact with the heater with the solid electrolyte body intervening therebetween, and
a surface area S of the outer electrode portion is 8% to 20% of a surface area T of a gas contact portion of the solid electrolyte body to be exposed to the gas to be measured.

2. The gas sensor as claimed in claim 1, wherein the outer partial electrode portion is disposed at such a position as to face the contact portion of the inner surface of the sensor element in contact with the heater with the solid electrolyte body intervening therebetween.

3. The gas sensor as claimed in claim 1, wherein as viewed from the direction of the axis, of angles formed by a line segment connecting two points at one circumferential end of the outer electrode portion and a center of the solid electrolyte body, and a line segment connecting two points at the other circumferential end of the outer electrode portion and the center, an angle in a region which contains the outer electrode portion is less than 180°.

4. The gas sensor as claimed in claim 1, wherein with respect to the direction of the axis, a length from a forward end of the gas contact portion to a rear end of the outer electrode portion is 40% or less of a length of the gas contact portion.

5. The gas sensor as claimed in claim 1, further comprising an inner electrode portion provided on an inner surface of a forward end portion of the solid electrolyte body,
wherein with respect to the direction of the axis, a rear end of the inner electrode portion is located rearward of a rear end of the outer electrode portion.

6. The gas sensor as claimed in claim 1, wherein the inner electrode portion has at least an inner partial electrode portion formed partially with respect to a circumferential direction of the inner surface, and the inner partial electrode portion is disposed at such a position as to face at least partially the outer partial electrode portion with the solid electrolyte body intervening therebetween.

7. The gas sensor as claimed in claim 1, wherein the heater is in contact with an inner side surface of an inner surface of the sensor element.

8. A gas sensor to be exposed to gas to be measured, comprising
a heater having a heat-generating portion formed of a heat-generating resistor
which generates heat through application of electricity,
a sensor element having
a closed-bottomed tubular solid electrolyte body having a closed forward end and extending in a direction of an axis,
an outer electrode portion provided on an outer surface of a forward end portion of the solid electrolyte body on a forward side of a rear end of the heat-generating portion with respect to the direction of the axis, and
an outer lead portion extending rearward from the outer electrode portion in the direction of the axis and having a width equal to a width of the outer electrode portion,
the gas sensor being characterized in that
the heater is in contact with an inner surface of the sensor element,
the outer electrode portion is formed partially with respect to a circumferential direction of the outer surface of the solid electrolyte body,
the outer electrode portion is disposed at such a position as to face a contact portion of the inner surface of the sensor element in contact with the heater with the solid electrolyte body intervening therebetween, and
a surface area S of the outer electrode portion is 8% to 20% of a surface area T of a gas contact portion of the solid electrolyte body to be exposed to the gas to be measured.

9. The gas sensor as claimed in claim 8, wherein as viewed from the direction of the axis, of angles formed by a line segment connecting two points at one circumferential end of the outer electrode portion and a center of the solid electrolyte body, and a line segment connecting two points at the other circumferential end of the outer electrode portion and the center, an angle in a region which contains the outer electrode portion is less than 180°.

10. The gas sensor as claimed in claim 8, wherein with respect to the direction of the axis, a length from a forward end of the gas contact portion to a rear end of the outer electrode portion is 40% or less of a length of the gas contact portion.

11. The gas sensor as claimed in claim 8, further comprising
an inner electrode portion provided on an inner surface of a forward end portion of the solid electrolyte body,
wherein with respect to the direction of the axis, a rear end of the inner electrode portion is located rearward of a rear end of the outer electrode portion.

12. The gas sensor as claimed in claim 8, wherein the inner electrode portion has at least an inner partial electrode portion formed partially with respect to a circumferential direction of the inner surface, and the inner partial electrode portion is disposed at such a position as to face at least partially the outer partial electrode portion with the solid electrolyte body intervening therebetween.

13. The gas sensor as claimed in claim 8, wherein the heater is in contact with an inner side surface of an inner surface of the sensor element.

* * * * *